(12) United States Patent
Biry et al.

(10) Patent No.: US 7,144,691 B2
(45) Date of Patent: Dec. 5, 2006

(54) COLOR PHOTOGRAPHIC RECORDING MATERIAL

(75) Inventors: Stéphane Biry, Village-Neuf (FR); Francesco Fuso, Therwil (CH); Andreas Kramer, Meyriez (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 39 days.

(21) Appl. No.: 10/504,240

(22) PCT Filed: Feb. 25, 2003

(86) PCT No.: PCT/EP03/01898

§ 371 (c)(1),
(2), (4) Date: Aug. 9, 2004

(87) PCT Pub. No.: WO03/075091

PCT Pub. Date: Sep. 12, 2003

(65) Prior Publication Data

US 2005/0079455 A1  Apr. 14, 2005

(30) Foreign Application Priority Data

Mar. 5, 2002   (EP)  ................................... 02405167

(51) Int. Cl.
| | | |
|---|---|---|
| G03C 1/46 | (2006.01) | |
| G03C 1/08 | (2006.01) | |
| G03C 7/26 | (2006.01) | |
| G03C 7/32 | (2006.01) | |
| G03C 1/06 | (2006.01) | |

(52) U.S. Cl. .................. 430/502; 430/543; 430/551; 430/556; 430/557; 430/600; 430/613

(58) Field of Classification Search ............... 430/551, 430/607
See application file for complete search history.

(56) References Cited

U.S. PATENT DOCUMENTS

| 4,517,283 A * | 5/1985 | Leppard et al. ............. 430/512 |
| 4,518,679 A * | 5/1985 | Leppard et al. ............. 430/372 |
| 4,518,688 A * | 5/1985 | Leppard et al. ............. 430/551 |
| 6,068,969 A * | 5/2000 | Mikoshiba et al. ......... 430/607 |

FOREIGN PATENT DOCUMENTS

| DE | 4426134 | 1/1996 |
| WO | 99/46261 | 9/1999 |

OTHER PUBLICATIONS

Derwent Abstr. 96-078096/09 for DE 4426134 (1996).

* cited by examiner

Primary Examiner—Geraldine Letscher
(74) Attorney, Agent, or Firm—Joseph C. Suhadolnik; Tyler A. Stevenson

(57) ABSTRACT

A color photographic material which contains on a support at least one blue-sensitive silver halide emulsion layer containing at least one yellow coupler, at least one green-sensitive silver halide emulsion layer containing at least one magenta coupler, at least one red-sensitive silver halide emulsion layer containing at least one cyan coupler, together with customary non-light-sensitive layers, characterized in that at least one layer contains a compound of formula (I) or (II) wherein the $R_1$-radicals and $R_2$-radicals are preferably methyl; and wherein the compounds of formula (II) are preferably (III) $R_3$ is a radical —CH(CH$_3$)—X—D, wherein X is phenylene. D is a group (IV) or a group —C(O)—C$_1$–C$_{18}$alkyl or a group —O—CH$_2$—CH(OH)—CH$_2$—NR$_{12}$R$_{13}$, with $R_{12}$ and $R_{13}$ being C$_1$–C$_{18}$alkyl or together form a 4 to 8 membered ring as defined in claim 1, or D is a group —O—CH$_2$—CH(OH)—CH$_2$—N(R$_{12}$)—CH$_2$—CHOH—CH$_2$—O—or        —O—CH$_2$—CH(OH)—CH$_2$—W—CH$_2$—CHOH—CH$_2$—O— with W being a divalent amino group (—N(C$_1$–C$_{18}$alkyl)–), a polyamine residue, a polyethyleneimine residue or a polyoxyalkyleneamine residue; Z and Z' are for example C$_1$–C$_{12}$alkyl, C$_3$–C$_{12}$alkenyl, C$_3$–C$_{12}$alkenyl, C$_5$–C$_8$cycloalkyl, or Z and Z' together bivalent groups such as —CH$_2$—CH$_2$— or —CH$_2$—C(R$_{18}$)(R$_{19}$)—CH(R$_{20}$)—

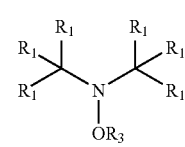

(I)

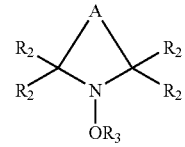

(II)

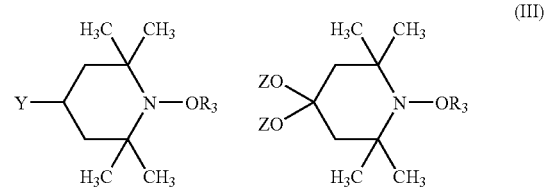

(III)

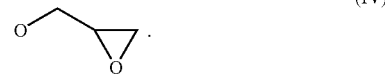

(IV)

12 Claims, No Drawings

COLOR PHOTOGRAPHIC RECORDING MATERIAL

The present invention relates to a colour photographic recording material with improved colour stability.

Colour photographic materials customarily contain at least one yellow coupler, at least one magenta coupler and at least one cyan coupler, from which the corresponding dyes are produced by exposure and development. These dyes should exhibit high stability upon prolonged dark storage or light exposure, in order to avoid premature deterioration of the photographic image. In particular, yellow dyes produced from couplers with an open-chain ketomethylene grouping must be stabilized both against light and dark fading. Various substances have already been proposed to achieve this object, e.g. bisphenol derivatives as disclosed in U.S. Pat. Nos. 3,700,455 and 4,782,011, epoxy compounds as taught in U.S. Pat. Nos. 5,316,903 and 5,183,731, phenolic thiane derivatives as reported in U.S. Pat. No. 5,070,007, and hindered amine compounds as disclosed in DE 2654058, U.S. Pat. No. 4,268,593 and RD 319902. However, the effect achieved with them is still inadequate and there is continued interest for more effective stabilizers.

It has now been found that certain glycidyl or alkylcarbonyl functional nitroxyl derivatives are able to provide yellow photographic dyes with outstanding resistance against light and dark fading.

The present invention thus pertains to a colour photographic material which contains on a support at least one blue-sensitive silver halide emulsion layer containing at least one yellow coupler, at least one green-sensitive silver halide emulsion layer containing at least one magenta coupler, at least one red-sensitive silver halide emulsion layer containing at least one cyan coupler, together with customary non-light-sensitive layers, characterized in that at least one layer contains a compound of the formula (I) or (II)

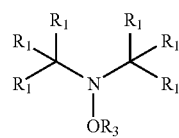
(I)

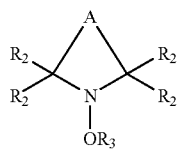
(II)

wherein
the $R_1$-radicals are each independently of one another hydrogen, halogen, $NO_2$, cyano, —$CONR_5R_6$, —$(R_9)COOR_4$, —$C(O)$—$R_7$, —$OR_8$, —$SR_8$, —$NHR_8$, —$N(R_8)_2$, carbamoyl, di($C_1$–$C_{18}$alkyl)carbamoyl, —$C(=NR_5)$(NHR_6)$;
unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_2$–$C_{12}$heterocycloalkyl; or
$C_1$–$C_{18}$alkyl, $C_2$–$C_{18}$alkenyl, $C_2$–$C_{18}$ alkynyl, $C_7$–$C_9$phenylalkyl, $C_3$–$C_{12}$ cycloalkyl or $C_2$–$C_{12}$heterocycloalkyl, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)-amino; or
phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino;
$R_4$ is hydrogen, $C_1$–$C_{18}$alkyl, phenyl, an alkali metal cation or a tetraalkyl-ammonium cation;
$R_5$ and $R_6$ are hydrogen, $C_1$–$C_{18}$alkyl, $C_2$–$C_{18}$alkyl, which is substituted by at least one hydroxy group or, taken together, form a $C_2$–$C_{12}$alkylene bridge or a $C_2$–$C_{12}$-alkylene bridge interrupted by at least one O or/and $NR_8$ atom;
$R_7$ is hydrogen, $C_1$–$C_{18}$alkyl or phenyl;
$R_8$ is hydrogen, $C_1$–$C_{18}$alkyl or $C_2$–$C_{18}$alkyl which is substituted by at least one hydroxy group;
$R_9$ is $C_1$–$C_{12}$alkylene or a direct bond; or
all the $R_1$-radicals form together the residue of a polycyclic cycloaliphatic ring system or a polycyclic heterocycloaliphatic ring system with at least one di- or trivalent nitrogen atom;
the $R_2$-radicals are independently of each other $C_1$–$C_6$alkyl or phenyl;
$R_3$ is a radical of the formula —$C(R_{10})(R_{10})$—$X$—$D$, wherein
X is phenylene, naphthylene or biphenylene, which are unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;
the $R_{10}$-radicals are independently of each other H or $CH_3$;
D is a group

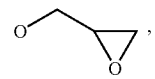, a group $C(O)$—$C_1$–$C_{18}$alkyl,
a group $C(O)$—$R_{11}$—$C(O)$—$C_1$–$C_{18}$alkyl; with $R_{11}$, being a bond or $C_1$–$C_{12}$alkylene, or
a group —$O$—$CH_2$—$CH(OH)$—$CH_2$—$NR_{12}R_{13}$, wherein
$R_{12}$ and $R_{13}$ independently of one another are unsubstituted $C_1$–$C_{18}$alkyl, $C_2$–$C_{18}$alkenyl, $C_2$–$C_{18}$alkynyl, phenyl, $C_7$–$C_9$phenylalkyl, $C_3$–$C_{12}$cycloalkyl; the radicals may be interrupted once or more than once by —, —$NH$—, —$O$—, —$S$—, —$CO$—, —$SO$—, —$SO_2$—, or
$C_1$–$C_{18}$alkyl, $C_2$–$C_{18}$alkenyl, $C_2$–$C_{18}$ alkynyl, phenyl, $C_7$–$C_9$phenylalkyl, $C_3$–$C_{12}$cycloalkyl, which are substituted by halogen, amino, hydroxy, carboxy, $C_1$–$C_6$alkoxy, $C_1$–$C_6$alkoxycarbonyl, $C_1$–$C_6$alkylthio, $C_1$–$C_6$alkylamino or di($C_1$–$C_6$alkyl)-amino, $C_1$–$C_6$alkylamino-carbonyl or di($C_1$–$C_6$alkyl)-amino-carbonyl; the radicals may be interrupted once or more than once by —, —$NH$—, —$O$—, —$S$—, —$CO$—, —$SO$—, —$SO_2$—, or
$R_{12}$ and $R_{13}$ together with N form a 4 to 8 membered ring, whereby the ring may be interrupted by —$O$—, —$NH$—, $S$—, —$CO$—, —$SO$—, —$SO_2$ and may be sustituted by carboxy, or
D is a group —$O$—$CH_2$—$CH(OH)$—$CH_2$—$N(R_{12})$—$CH_2$—$CHOH$—$CH_2$—$O$— or $O$—$CH_2$—$CH(OH)$—$CH_2$—$W$—$CH_2$—$CHOH$—$CH_2$—$O$— with W being a divalent amino group (—N(R$_{12}$)-), a polyamine residue, a polyethyleneimine residue or a polyoxyalkyleneamine residue;

A is a divalent group required to form a cyclic 5-, 6- or 7-membered ring, whereby the divalent group is selected from C$_2$–C$_4$alkylene, C$_2$–C$_4$alkenylene, C$_2$–C$_4$alkinylene, 1,2 phenylene which may be unsubstituted or substituted by NO$_2$, halogen, amino, hydroxy, cyano, carboxy, carbonyl, C$_1$–C$_{18}$alkoxy, C$_1$–C$_{18}$ acyloxy, benzoyloxy, C$_1$–C$_{18}$alkylthio, C$_1$–C$_{18}$alkylamino or di(C$_1$–C$_{18}$alkyl)amino, or phenyl; or A is a group —CH$_2$—CHY—CH$_2$—, wherein Y is H, OH, OR$_{14}$, NR$_{15}$R$_{16}$, —O—C(O)—R$_{17}$ or NR$_{15}$—C(O)—R$_{17}$;

R$_{14}$ is C$_1$–C$_{18}$alkyl, C$_2$–C$_{18}$alkenyl, C$_2$–C$_{18}$alkenyl, phenyl, benzyl, mesityl, or C$_2$–C$_{18}$alkyl which is substituted by at least one hydroxy group;

R$_{15}$ and R$_{16}$ independently are hydrogen, C$_1$–C$_{18}$alkyl, C$_2$–C$_{18}$alkenyl, C$_2$–C$_{18}$alkenyl, or taken together form a C$_2$–C$_{12}$alkylene bridge or a C$_2$–C$_{12}$alkylene bridge interrupted by at least one O atom;

R$_{17}$ is phenyl, benzyl, mesityl, C$_1$–C$_{18}$alkyl, C$_2$–C$_{18}$alkenyl, C$_2$–C$_{18}$alkinyl; or A is a group —CH$_2$—C(OZ)(OZ')—CH$_2$—, wherein Z and Z' are independently C$_1$–C$_{12}$alkyl, C$_3$–C$_{12}$alkenyl, C$_3$–C$_{12}$alkinyl, C$_5$–C$_8$cycloalkyl, phenyl, naphthyl, C$_7$–C$_9$phenylalkyl; or Z and Z' together form one of the bivalent groups —C(R$_{18}$)(R$_{19}$)—CH(R$_{20}$)—, CH(R$_{18}$)—CH$_2$—C(R$_{19}$)(R$_{20}$)—, —CH(R$_{19}$)—CH$_2$—C(R$_{18}$)(R$_{20}$)—, —CH$_2$—C(R$_{18}$)(R$_{19}$)—CH(R$_{20}$)—, o-phenylene, 1,2-cyclohexylidene, —CH$_2$—CH=CH—CH$_2$— or

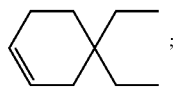

wherein

R$_{18}$ is hydrogen, C$_1$–C$_{18}$alkyl, COOH, COO—(C$_1$–C$_{18}$)alkyl, OCO—(C$_1$–C$_{18}$)alkyl or CH$_2$OR$_{21}$;

R$_{19}$ and R$_{20}$ are independently hydrogen, C$_1$–C$_{12}$alkyl, COOH or COO—(C$_1$–C$_{12}$)-alkyl;

R$_{21}$ is hydrogen, C$_1$–C$_{18}$alkyl, C$_5$–C$_6$cycloalkyl, benzyl, or a monovalent acyl residue derived from an aliphatic, cycloaliphatic or aromatic monocarboxylic acid having up to 18 carbon atoms; or Z and Z' together form one of the tetravalent groups

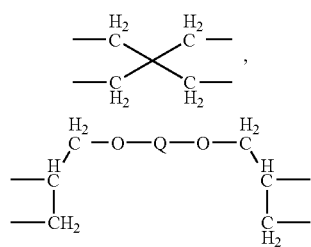

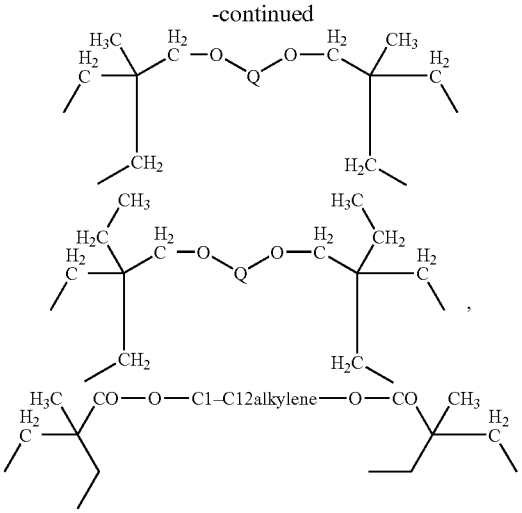

wherein

Q is a bisacyl residue which is derived from a C$_2$–C$_{12}$dicarboxylic acid or C$_1$–C$_{12}$alkylene.

DEFINITIONS

Halogen is fluoro, chloro, bromo or iodo.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

The alkenyl radicals in the various substituents may be linear or branched. Examples of C$_2$–C$_{18}$alkenyl are vinyl, allyl, 2-methylallyl, butenyl, hexenyl, undecenyl and octadecenyl. Preferred alkenyls are those, wherein the carbon atom in the 1-position is saturated and where the double bond is not activated by substituents like O, C=O, and the like.

Examples of C$_2$–C$_{18}$alkynyl are ethynyl, 2-butynyl, 3-hexynyl, 5-undecynyl, 6-octadecynyl. The alkynyl radicals may be linear or branched.

C$_7$–C$_9$phenylalkyl is for example benzyl, phenylpropyl, a,a-dimethylbenzyl or a-methylbenzyl.

C$_3$–C$_{12}$cycloalkyl which is unsubstituted or substituted by 1, 2 or 3 C$_1$–C$_4$alkyl is e.g. cyclopropyl, cyclopentyl, methylcyclopentyl, dimethylcyclopentyl, cyclohexyl, methylcyclohexyl.

Alkyl substituted by —OH is typically 2-hydroxyethyl, 2-hydroxypropyl or 2-hydroxybutyl. C$_1$–C$_{18}$Alkyl substituted by C$_1$–C$_8$alkoxy, preferably by C$_1$–C$_4$alkoxy, in particular by methoxy or ethoxy, is typically 2-methoxyethyl, 2-ethoxyethyl, 3-methoxypropyl, 3-ethoxypropyl, 3-butoxypropyl, 3-octoxypropyl and 4-methoxybutyl.

C$_1$–C$_{18}$Alkyl substituted by di(C$_1$–C$_4$alkyl)amino is preferably e.g. dimethylamino, diethylamino, 2-dimethylaminoethyl, 2-diethylaminoethyl, 3-dimethylaminopropyl, 3-diethylaminopropyl, 3-dibutylaminopropyl and 4-diethylaminobutyl.

C$_1$–C$_{18}$Alkyl substituted by C$_1$–C$_4$alkylamino is preferably e.g. methylamino, ethylamino, 2-methylaminoethyl, 2-ethylaminoethyl, 3-methylaminopropyl, 3-ethylaminopropyl, 3-butylaminopropyl and 4-ethylaminobutyl.

$C_1$–$C_8$Alkoxy and, preferably $C_1$–$C_4$alkoxy, are typically methoxy, ethoxy, propoxy, isopropoxy, butoxy, isobutoxy, pentoxy, isopentoxy, hexoxy, heptoxy or octoxy. $C_1$–$C_4$Alkylthio is typically thiomethyl, thioethyl, thiopropyl, thioisopropyl, thiobutyl and thioisobutyl.

$C_2$–$C_{12}$Heterocycloalkyl is typically oxirane, 1,4-dioxane, tetrahydrofuran, γ-butyrolactone, ε-caprolactam, oxirane, aziridine, diaziridine, pyrrole, pyrrolidine, thiophen, furan, pyrazole, imidazole, oxazole, oxazolidine, thiazole, pyran, thiopyran, piperidine or morpholine.

Examples of $C_2$–$C_{12}$alkylene bridges, preferably of $C_2$–$C_6$alkylene bridges, are ethylene, propylene, butylene, pentylene, hexylene.

$C_2$–$C_{12}$alkylene bridges interrupted by at least one N or O atom are, for example, —$CH_2$—O—$CH_2$—$CH_2$—, —$CH_2$—O—$CH_2$—$CH_2$—$CH_2$—, —$CH_2$—O—$CH_2CH_2$—$CH_2$—$CH_2$—, —$CH_2$—O—$CH_2$—$CH_2$—O—$CH2$—, —$CH_2$—NH—$CH_2$—$CH_2$—, —$CH_2$—NH—$CH_2$—$CH_2$—$CH_2$—, —$CH_2$—NH—$CH_2$—$CH_2$—$CH_2$—$CH_2$—, —$CH_2$—NH—$CH_2$—$CH_2$—NH—$CH2$— or —$CH_2$—NH—$CH_2$—$CH_2$—O—$CH_2$—. Alkenyl having from 3 to 12 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl, isododecenyl.

Alkinyl having from 3 to 12 carbon atoms is a branched or unbranched radical, for example propinyl (—$CH_2$—C≡CH), 2-butinyl, 3-butinyl, n-2-octinyl or n-2-dodecinyl.

$C_7$–$C_9$phenylalkyl is for example benzyl, α-methylbenzyl, α,α-dimethylbenzyl or 2-phenylethyl, benzyl is preferred.

$C_1$–$C_{12}$alkylene is a branched or unbranched radical, for example methylene, ethylene, propylene, trimethylene, tetramethylene, pentamethylene, hexamethylene, heptamethylene, octamethylene, decamethylene or dodecamethylene.

$C_5$–$C_8$cycloalkyl is for example cyclopentyl, cyclohexyl, cycloheptyl, methylcyclopentyl or cyclooctyl.

Examples of a monocarboxylic acid having up to 18 carbon atoms are formic acid, acetic acid, propionic acid, the isomers of valeric acid, methyl ethyl acetic acid, trimethyl acetic acid, capronic acid, lauric acid or stearic acid. Examples for unsaturated aliphatic acids are acrylic acid, methacrylic acid, crotonic acid, linolic acid and oleic acid.

Typical examples of cycloaliphatic carboxylic acids are cyclohexane carboxylic acid or cyclopentane carboxylic acid.

Examples of aromatic carboxylic acids are benzoic acid, salicylic acid or cinnamic acid.

Examples of dicarboxylic acids are oxalic acid, malonic acid, succinic acidglutaric acid adipic acid, sebatic acid, fumaric acid, maleic acid, phthalic acid, isophthalic acid, terephthalic acid.

Examples for $C_4$–$C_{12}$cycloalkanone-yl are cyclopentanone-yl, cyclohexanone-yl or cycloheptanone-yl.

Phenyl substituted by 1, 2 or 3 $C_1$–$C_4$alkyl or $C_1$–$C_4$alkoxy is typically methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of polycyclic cycloaliphatic ring systems are adamantane, cubane, twistane, norbornane, bicyclo[2.2.2]octane or bicyclo[3.2.1]octane.

An example of a polycyclic heterocycloaliphatic ring system is hexamethylentetramine (urotropine).

Examples of a bisacyl residue which is derived from a $C_2$–$C_{12}$dicarboxylic acid are: —(O)C—$(CH_2)_{1-6}$—C(O)—, —(O)C-phenylene-C(O)—.

Concerning the group W, examples for polyamines are ethylenediamine, N-methylethylenediamine, N,N'-dimethylethylenediamine, N-methyl-1,3-propanediamine, N,N'-dimethyl-1,3-propanediamine, N,N'-dimethyl-1,6-hexanediamine, diethylenetriamine, 3,3'-imino-bis-propylamine, spermidine, bis(hexamethylene)triamine, triethylenetetramine, N,N'-Bis(3-aminopropyl)-ethylenediamine, spermine, tris(2-aminoethyl)amine, tetraethylenepentamine, pentaethylenehexamine, 4,4'-methylenebis(cyclohexylamine), 1,4-diaminocyclohexane, N-cyclo-hexyl-1,3-propanediamine, 1,8-diamino-p-menthane, N,N'-diethyl-2-butene-1,4-diamine, 2,2'-oxy-bis(ethylamine), 4,7,10-trioxa-1,13-tridecanediamine, N,N'-bis(2-hydroxyethyl)ethylenediamine, 4,4'-bipiperidine, piperazine, 1,4,7-triazacyclononane, 1,3-diaminoaceton, 1,4-phenylendiamine, N,N'-dibenzylethylenediamine or m-xylylenediamine.

Polyoxyalkyleneamines are amine terminated polyethers and refer to monoamine, diamine, or triamines. They are commercially available under the tradename JEFFAMINE™ from Huntsman Corp. Zaventem, Belgium.

Examples for the group D being —O—$CH_2$—CH(OH)—$CH_2$—$NR_{12}R_{13}$, wherein $R_{12}$ and $R_{13}$ together with N form a 4 to 8 membered ring, are:

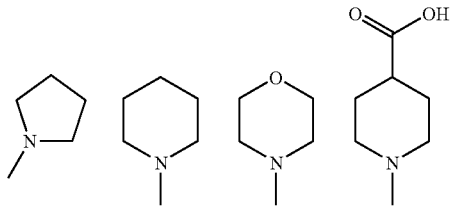

When the divalent group A has the meaning of $C_2$–$C_4$alkylene or $C_2$–$C_4$alkenylene, these groups may also be interrupted by an O or N atom.

$C_2$–$C_4$alkylene bridges interrupted by at least one N, O atom are, for example, —$CH_2$—O—$CH_2$—$CH_2$—, —$CH_2$—O—$CH_2$—, —O—$CH_2$—$CH_2$—, —O—$CH_2$—O—$CH2$—, —$CH_2$—NH—$CH_2$—, —$CH_2$NH—$CH_2$—$CH_2$—, —NH—$CH_2$—$CH_2$—, —NH—$CH_2$—NH—$CH2$— or —$CH_2$—NH—$CH_2$—.

Preferred Compounds I

Preferred are compounds of the formula (I), wherein the group

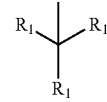

is

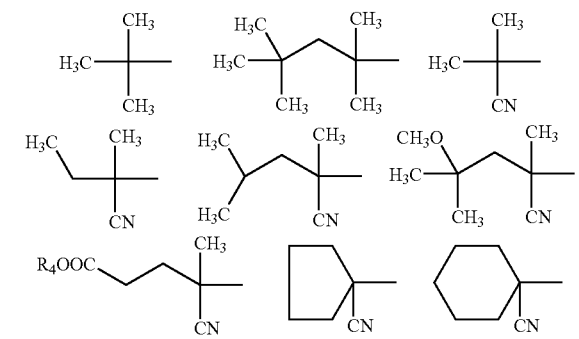

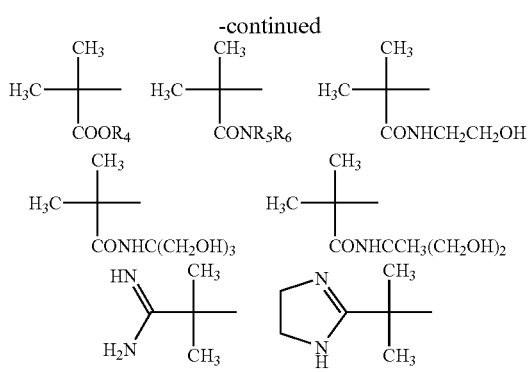

Most preferred are compounds of the formula I, wherein all $R_1$ radicals are methyl and
$R_3$ is a radical —CH(CH$_3$)—X—D wherein X is phenylene, D is a group

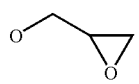

or a group —C(O)—$C_1$–$C_{18}$alkyl or a group —O—CH$_2$—CH(OH)—CH$_2$—NR$_{12}$R$_{13}$, with $R_{12}$ and $R_{13}$ being $C_1$–$C_{18}$alkyl or together form a 4 to 8 membered ring as defined above, or D is a group —O—CH$_2$—CH(OH)—CH$_2$—N(R$_{12}$)—CH$_2$—CHOH—CH$_2$—O— or —O—CH$_2$—CH(OH)—CH$_2$—W—CH$_2$—CHOH—CH$_2$—O— with W being a divalent amino group (—N($C_1$–$C_{18}$alkyl)-), a polyamine residue, a polyethyleneimine residue or a polyoxyalkyleneamine residue.

An example of a suitable compound of formula (I) is

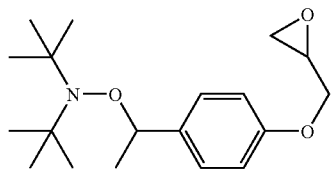

Compounds IIa

Compound IIa is a compound II wherein $R_2$ is methyl and A is a group —CH$_2$—CHY—CH$_2$—

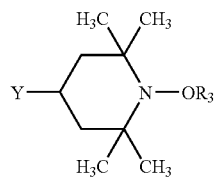

Y and $R_3$ are as defined above.

Preferred Compounds IIa

Preferred are compounds of the formula IIa, wherein
Y is H, OH, OR$_{14}$, —O—C(O)—R$_{17}$;
$R_{14}$ is $C_1$–$C_{18}$alkyl, phenyl, benzyl, mesityl,
$R_{17}$ is $C_1$–$C_{18}$alkyl, phenyl, benzyl, mesityl,
$R_3$ is a radical —CH(CH$_3$)—X—D wherein X is phenylene,
D is a group

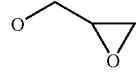

or a group —C(O)—$C_1$–$C_{18}$alkyl or a group —O—CH$_2$—CH(OH)—CH$_2$—NR$_{12}$R$_{13}$, with $R_{12}$ and $R_{13}$ being $C_1$–$C_{18}$alkyl or together form a 4 to 8 membered ring as defined above, or D is a group —O—CH$_2$—CH(OH)—CH$_2$—N(R$_{12}$)—CH$_2$—CHOH—CH$_2$—O— or —O—CH$_2$—CH(OH)—CH$_2$—W—CH$_2$—CHOH—CH$_2$—O— with W being a divalent amino group (—N($C_1$–$C_{18}$alkyl)-), a polyamine residue, a polyethyleneimine residue or a polyoxyalkyleneamine residue.

Examples of compounds of the formula IIa

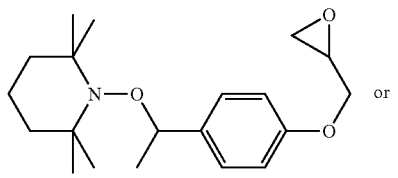 or

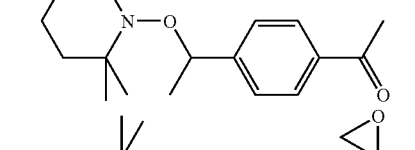

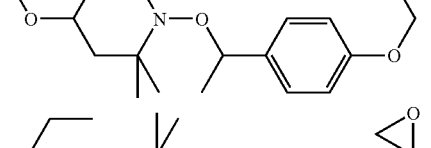 or

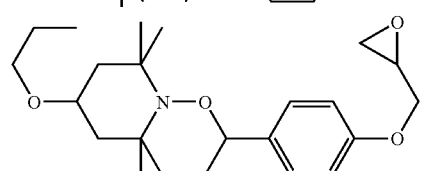

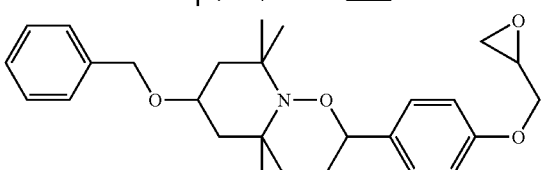

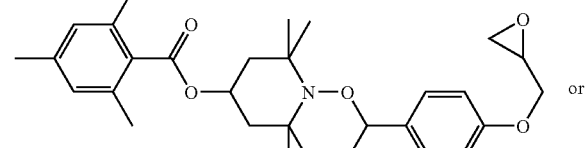 or

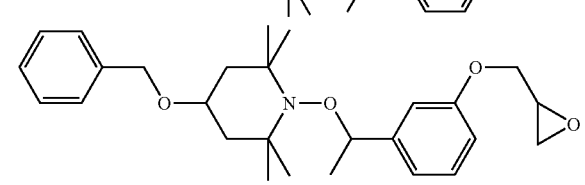

-continued

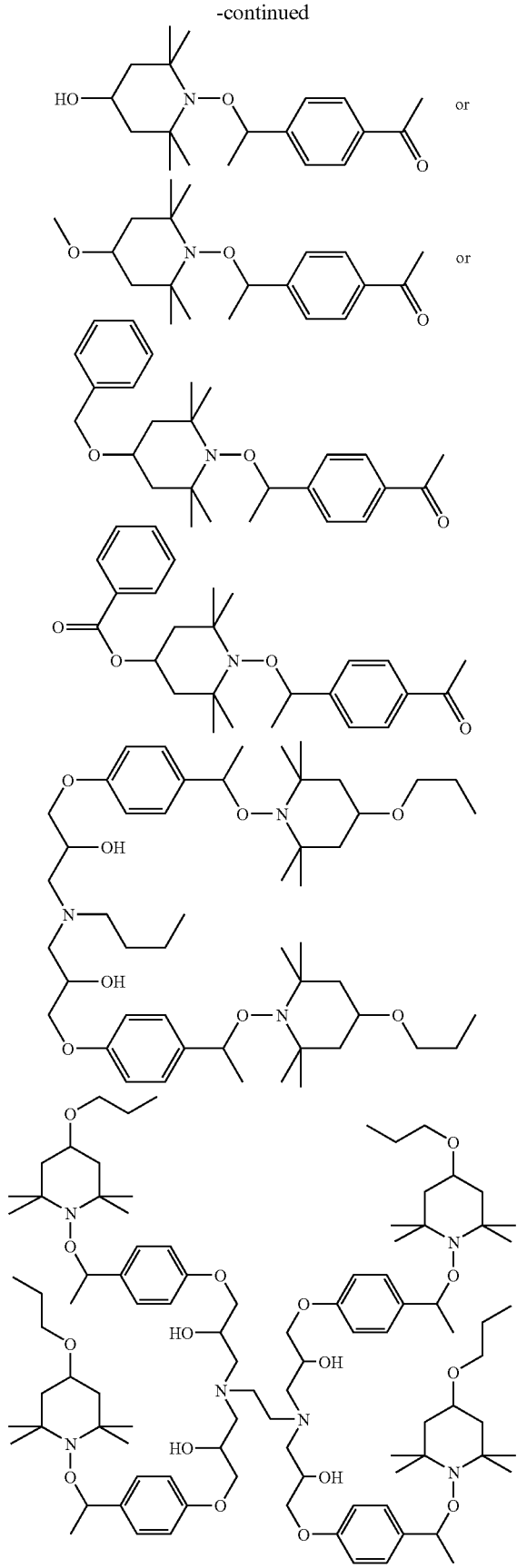

Compounds IIb.

Compound IIb is a compound II, wherein $R_2$ is methyl and A is a group

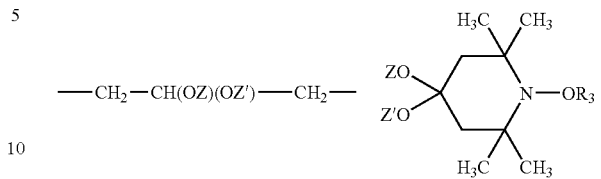

Z, Z' and $R_3$ are as defined above.

Preferred are compounds of the formula IIb are those wherein $R_3$ is a radical —CH(CH$_3$)—X—D wherein X is phenylene, D is a group

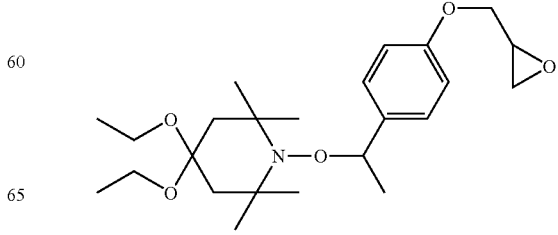

or a group —C(O)—C$_1$–C$_{18}$alkyl or a group —O—CH$_2$—CH(OH)—CH$_2$—NR$_{12}$R$_{13}$, with R$_{12}$ and R$_{13}$ being C$_1$–C$_{18}$alkyl or together form a 4 to 8 membered ring as defined above, or D is a group —O—CH$_2$—CH(OH)—CH$_2$—N(R$_{12}$)—CH$_2$—CHOH—CH$_2$—O— or O—CH$_2$—CH(OH)—CH$_2$—W—CH$_2$—CHOH—CH$_2$—O— with W being a divalent amino group (—N(C$_1$–C1$_8$alkyl)-), a polyamine residue, a polyethyleneimine residue or a polyoxyalkyleneamine residue.

Examples of compounds IIb, wherein Z and Z' are the same radicals and are C$_1$–C$_{12}$alkyl, C$_3$–C$_{12}$alkenyl, C$_5$–C$_8$cycloalkyl, benzyl; and R$_3$ is —CH(CH$_3$)—X—D, X is phenylene, are:

1.) 4,4-Dimethoxy-2,2,6,6-tetramethyl-1-[1-(4-oxiranyl-methoxy-phenyl)-ethoxy]-piperidine 2.) 4,4-Diethoxy-2,2,6,6-tetramethyl-1-[1-(4-oxiranyl-methoxy-phenyl)-ethoxy]-piperidine 3.) 2,2,6,6-Tetramethyl-1-[1-(4-oxiranylmethoxy-phenyl)-ethoxy]-4,4-dipropoxy-piperidine

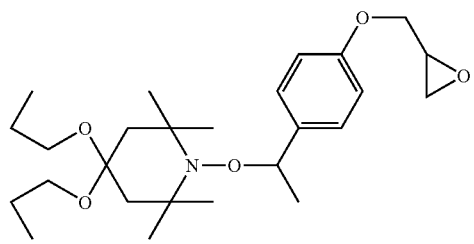

4.) 4,4-Dibutoxy-2,2,6,6-tetramethyl-1-[1-(4-oxiranyl-methoxy-phenyl)-ethoxy]-piperidine

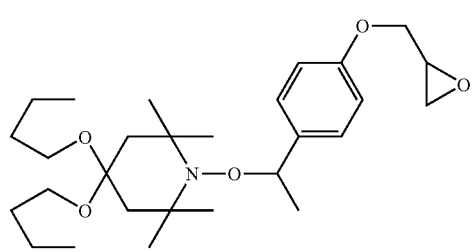

5.) 4,4-Diisobutoxy-2,2,6,6-tetramethyl-1-[1-(4-oxiranyl-methoxy-phenyl)-ethoxy]-piperidine

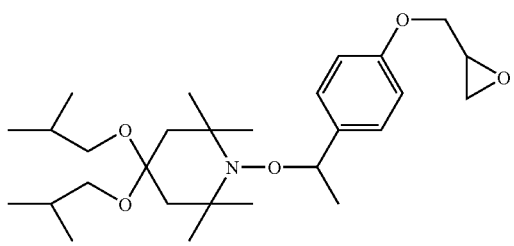

6.) 2,2,6,6-Tetramethyl-4,4-bis-octyloxy-1-[1-(4-oxiranyl-methoxy-phenyl)-ethoxy]-piperidine

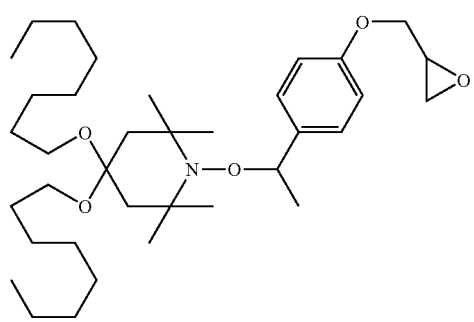

7.) 4,4-Bis-allyloxy-2,2,6,6-tetramethyl-1-[1-(4-oxiranyl-methoxy-phenyl)-ethoxy]-piperidine

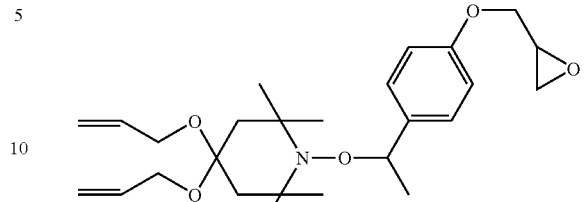

8.) 4,4-Bis-cyclohexyloxy-2,2,6,6-tetramethyl-1-[1-(4-oxiranylmethoxy-phenyl)-ethoxy]-piperidine

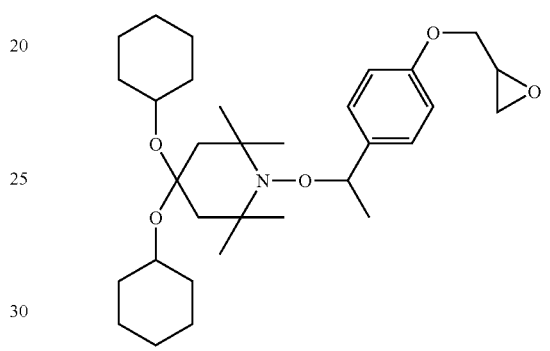

9.) 4,4-Bis-benzyloxy-2,2,6,6-tetramethyl-1-[1-(4-oxiranyl-methoxy-phenyl)-ethoxy]-piperidine

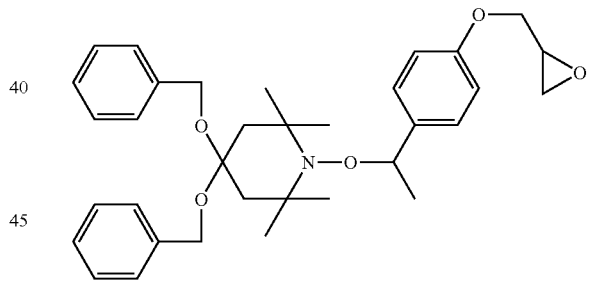

Examples of compounds IIb, wherein Z and Z' together form one of the bivalent groups —C(R$_{18}$)(R$_{19}$)—CH(R$_2$O)— or o-phenylene or 1,2-cyclohexylidene and R$_3$ is —CH(CH$_3$)—X—D, X is phenylene, are:

1.) 7,7,9,9-Tetramethyl-8-[1-(4-oxiranylmethoxy-phenyl)-ethoxy]-1,4-dioxa-8-aza-spiro[4.5]decane

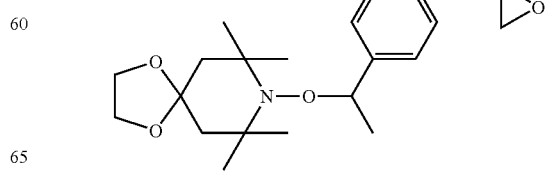

2.) 2,7,7,9,9-Pentamethyl-8-[1-(4-oxiranylmethoxy-phenyl)-ethoxy]-1,4-dioxa-8-aza-spiro[4.5]decane

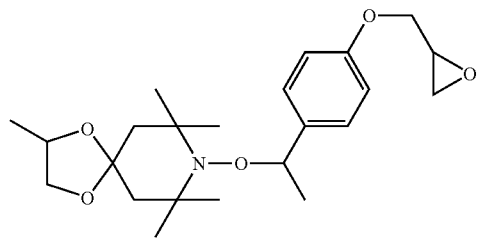

3.) 2-Ethyl-7,7,9,9-tetramethyl-8-[1-(4-oxiranylmethoxy-phenyl)-ethoxy]-1,4-dioxa-8-aza-spiro[4.5]decane

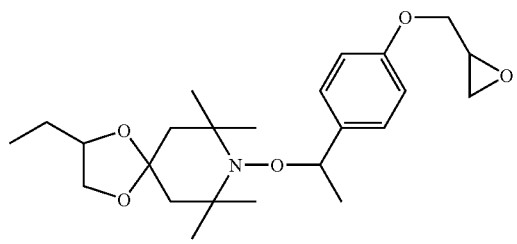

4.) 7,7,9,9-Tetramethyl-8-[1-(4-oxiranylmethoxy-phenyl)-ethoxy]-2-propyl-1,4-dioxa-8-aza-spiro[4.5]decane

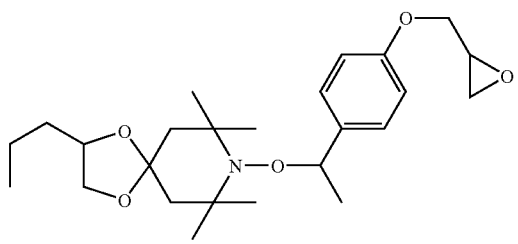

5.) 2-Butyl-7,7,9,9-tetramethyl-8-[1-(4-oxiranylmethoxy-phenyl)-ethoxy]-1,4-dioxa-8-aza-spiro[4.5]decane

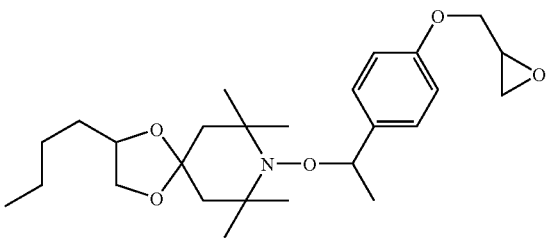

6.) 7,7,9,9-Tetramethyl-2-octyl-8-[1-(4-oxiranylmethoxy-phenyl)-ethoxy]-1,4-dioxa-8-aza-spiro[4.5]decane

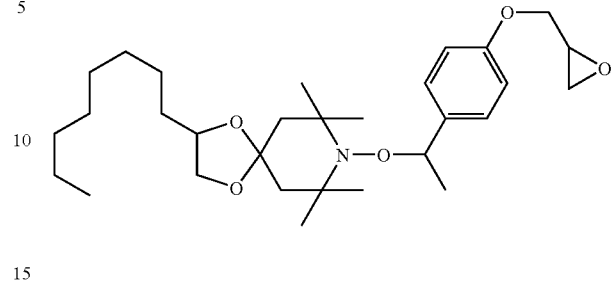

7.) 2-Decyl-7,7,9,9-tetramethyl-8-[1-(4-oxiranylmethoxy-phenyl)-ethoxy]-1,4-dioxa-8-aza-spiro[4.5]decane

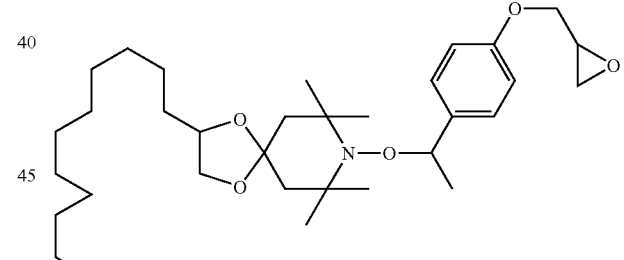

8.) 2-Dodecyl-7,7,9,9-tetramethyl-8-[1-(4-oxiranyl-methoxy-phenyl)-ethoxy]-1,4-dioxa-8-aza-spiro[4.5]decane 9.) (7,7,9,9-Tetramethyl-8-[1-(4-oxiranylmethoxy-phenyl)-ethoxy]-1,4-dioxa-8-aza-spiro[4.5]dec-2-yl)-methanol

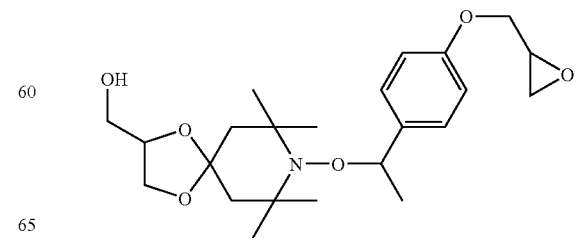

10.) 2-Methoxymethyl-7,7,9,9-tetramethyl-8-[1-(4-oxiranylmethoxy-phenyl)-ethoxy]-1,4-dioxa-8-aza-spiro[4.5]decane

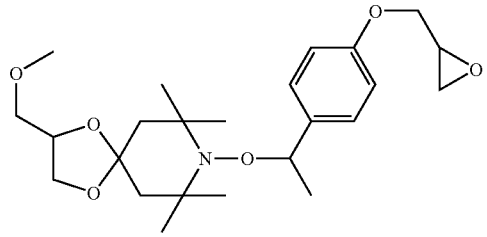

11.) 2–Cyclohexyloxymethyl-7,7,9,9-tetramethyl-8-[1-(4-oxiranylmethoxy-phenyl)-ethoxy]-1,4-dioxa-8-aza-spiro[4.5]decane

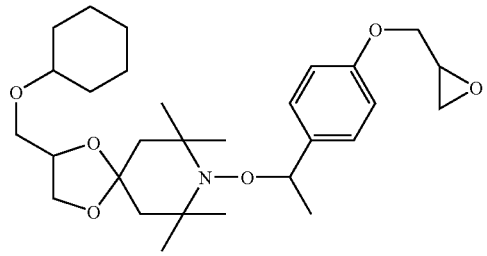

12.) 2-Benzyloxymethyl-7,7,9,9-tetramethyl-8-[1-(4-oxiranylmethoxy-phenyl)-ethoxy]-1,4-dioxa-8-aza-spiro[4.5]decane

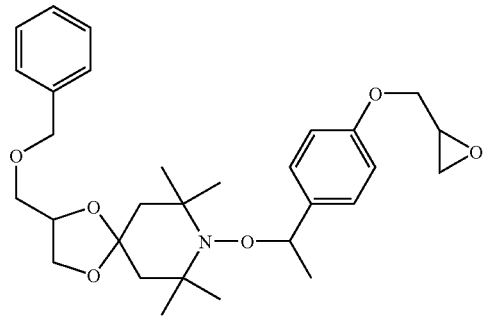

13.) Acetic acid 7,7,9,9-tetramethyl-8-[1-(4-oxiranylmethoxy-phenyl)-ethoxy]-1,4-dioxa-8-aza-spiro4.5]dec-2-ylmethyl ester

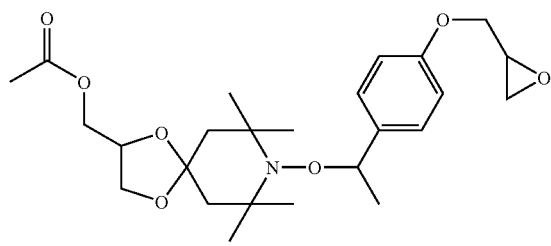

14.) Octadecanoic acid 7,7,9,9-tetramethyl-8-[1-(4-oxiranylmethoxy-phenyl)-ethoxy]-1,4-dioxa-8-aza-spiro[4.5]dec-2-ylmethyl ester

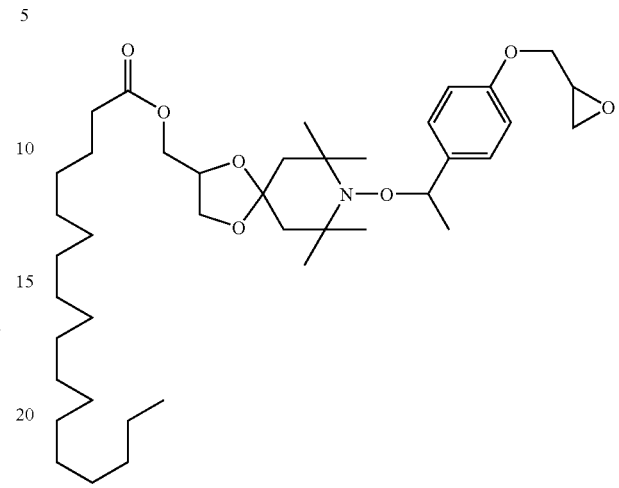

15.) Benzoic acid 7,7,9,9-tetramethyl-8-[1-(4-oxiranylmethoxy-phenyl)-ethoxy]-1,4-dioxa-8-aza-spiro[4.5]dec-2-ylmethyl ester

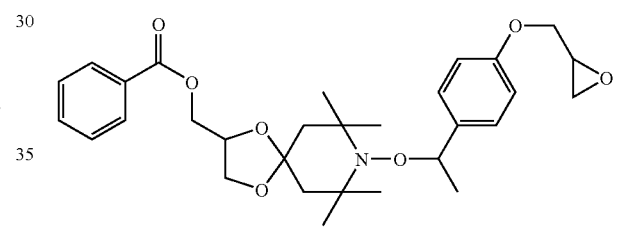

16.) 2,2,7,7,9,9-Hexamethyl-8-[1-(4-oxiranylmethoxy-phenyl)-ethoxy]-1,4-dioxa-8-aza-spiro[4.5]decane

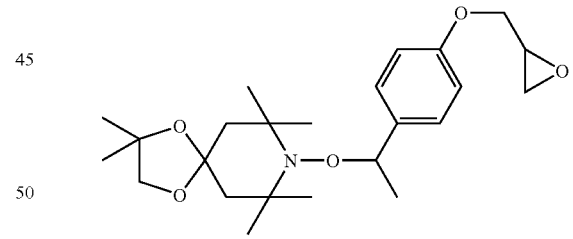

17.) 2,3,7,7,9,9-Hexamethyl-8-[1-(4-oxiranylmethoxy-phenyl)-ethoxy]-1,4-dioxa-8-aza-spiro[4.5]decane

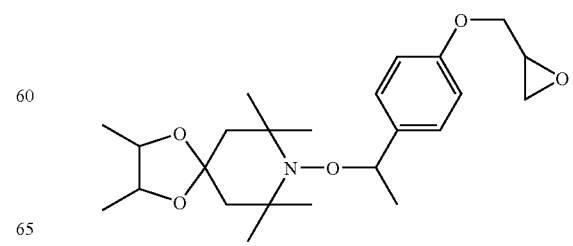

18.) 4,4-(o-Phenylendioxy)-2,2,6,6-tetramethyl-1-[1'-(4'-oxiranylmethoxy-phenyl)-ethoxy]-piperidine

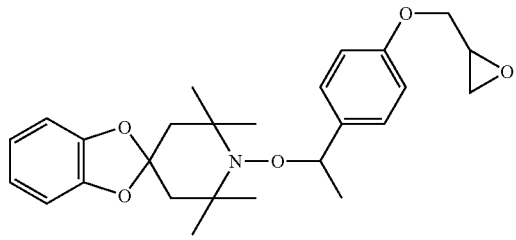

19.) 4,4-(1',2'-cyclohexylendioxy)-2,2,6,6-tetramethyl-1-[1''-(4''-oxiranylmethoxy-phenyl)-ethoxy]-piperidine

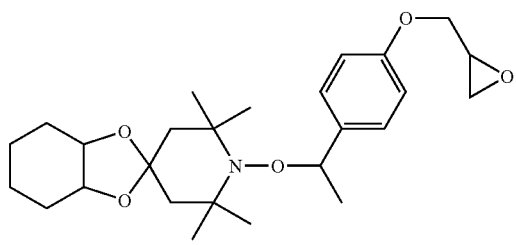

20.) 7,7,9,9-Tetramethyl-8-[1-(4-oxiranylmethoxy-phenyl)-ethoxy]-1,4-dioxa-8-aza-spiro[4.5]decane-2,3-dicarboxylic acid dimethyl ester

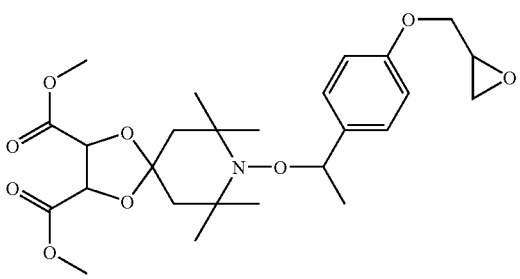

Examples of compounds IIb, wherein Z and Z' together form one of the bivalent groups —CH$_2$—C(R$_{18}$)(R$_{19}$)—CH(R$_{20}$)—, o-phenylene or 1,2-cyclohexylidene, —CH$_2$—CH=CH—CH$_2$— or

and R$_3$ is —CH(CH$_3$)—X—D, X is phenylene, are:
1.) 8,8,10,10-Tetramethyl-9-[1-(4-oxiranylmethoxy-phenyl)-ethoxy]-1,5-dioxa-9-aza-spiro[5.5]undecane

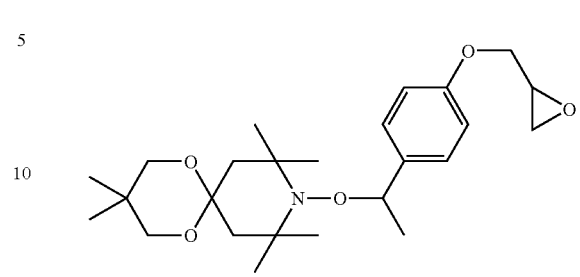

2.) 3,3,8,8,10,10-Hexamethyl-9-[1-(4-oxiranylmethoxy-phenyl)-ethoxy]-1,5-dioxa-9-aza-spiro[5.5]undecane

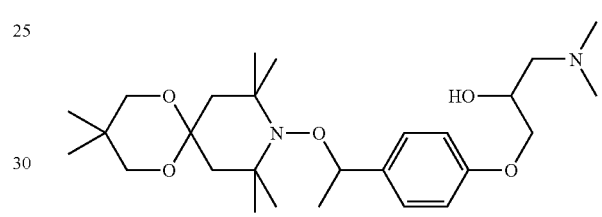

3.) 1-Dimethylamino-3-{4-[1-(3,3,8,8,10,10-hexamethyl-1,5-dioxa-9-aza-spiro[5.5undec-9-yloxy)-ethyl]-phenoxy}-propan-2-ol1-Dimethylamino-3-{4-[1-(3,3,8,8,10,10-hexamethyl-1,5-dioxa-9-aza-spiro[5.5]undec-9-yloxy)-ethyl]-phenoxy}-propan-2-ol

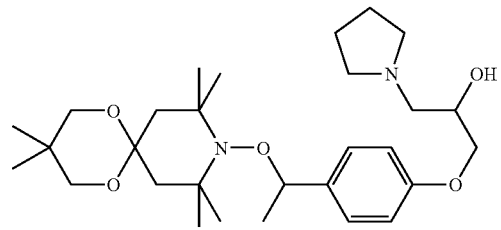

4.) 1-{4-[1-(3,3,8,8,10,10-Hexamethyl-1,5-dioxa-9-aza-spiro[5.5]undec-9-yloxy)-ethyl]-phenoxy}-3-pyrrolidin-1-yl-propan-2-ol

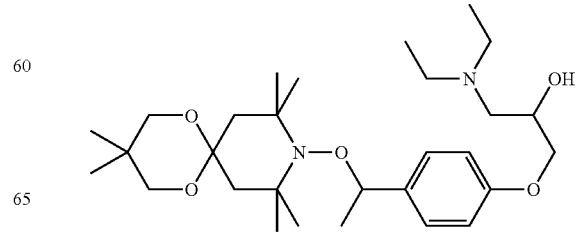

5.) 1-Diethylamino-3-{4-[1-(3,3,8,8,10,10-hexamethyl-1,5-dioxa-9-aza-spiro[5.5]undec-9-yloxy)-ethyl]-phenoxy}-propan-2-ol 6.) 3-Ethyl-3,8,8,10,10-pentamethyl-9-[1-(4-oxiranyl-methoxy-phenyl)-ethoxy]-1,5-dioxa-9-aza-spiro[5.5]un-decane

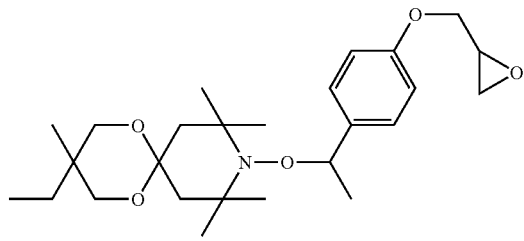

7.) 3,3-Diethyl-8,8,10,10-tetramethyl-9-[1-(4-oxiranyl-methoxy-phenyl)-ethoxy]-1,5-dioxa-9-aza-spiro[5.5]un-decane

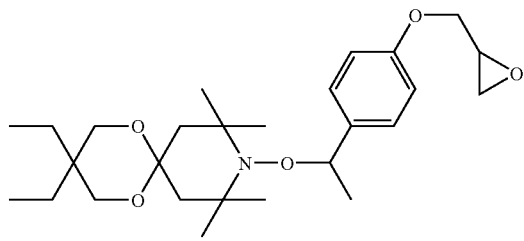

8.) 3,8,8,10,10-Pentamethyl-9-[1-(4-oxiranylmethoxy-phenyl)-ethoxy]-3-propyl-1,5-dioxa-9-aza-spiro[5.5]unde-cane

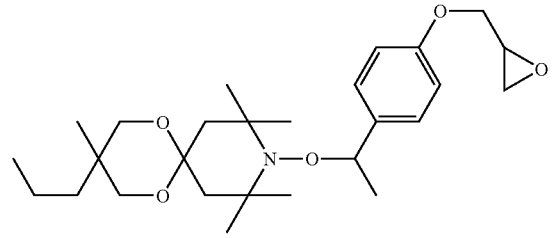

9.) 3-Butyl-3-ethyl-8,8,10,10-tetramethyl-9-[1-(4-oxiranyl-methoxy-phenyl)-ethoxy]-1,5-dioxa -9-aza-spiro[5.5]un-decane

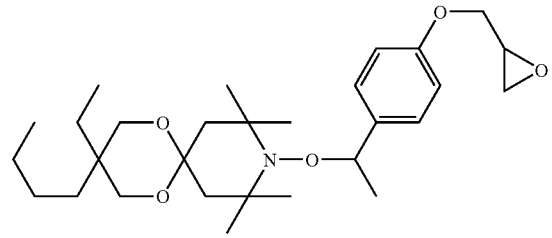

10.) 2,2,4,4-Tetramethyl-3-[1-(4-oxiranylmethoxy-phenyl)-ethoxy]-7,16-dioxa-3-aza-dispiro[5.2.5.2]hexadec-11-ene

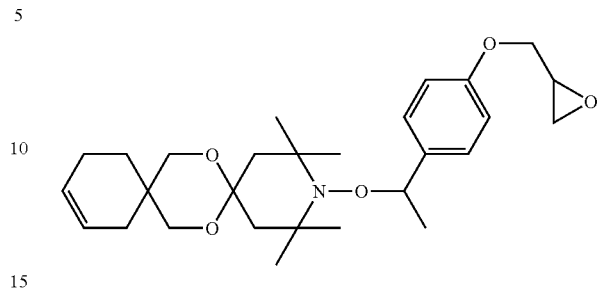

11.) {3,8,8,10,10-Pentamethyl-9-[1-(4-oxiranylmethoxy-phenyl)-ethoxy]-1,5-dioxa-9-aza-spiro[5.5]undec-3-yl}-methanol

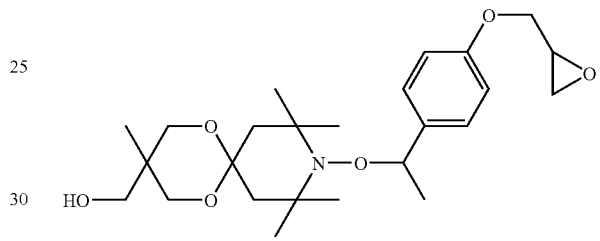

12.) {3-Ethyl-8,8,10,10-tetramethyl-9-[1-(4-oxiranyl-methoxy-phenyl)-ethoxy]-1,5-dioxa-9-aza-spiro[5.5]un-dec-3-yl}-methanol

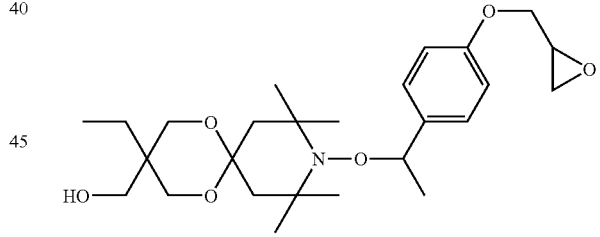

13.) 3-Methoxymethyl-3,8,8,10,10-pentamethyl-9-[1-(4-ox-iranylmethoxy-phenyl)-ethoxy]-1,5-dioxa-9-aza-spiro[5.5]undecane

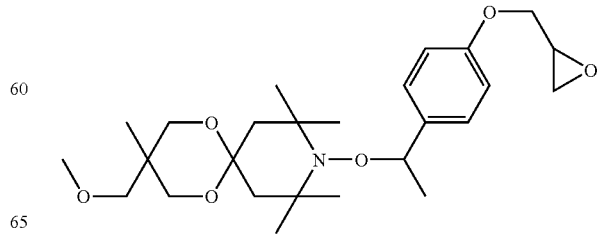

14.) 3-Cyclohexyloxymethyl-3,8,8,10,10-pentamethyl-9-[1-(4-oxiranylmethoxy-phenyl)-ethoxy]-1,5-dioxa-9-aza-spiro[5.5]undecane

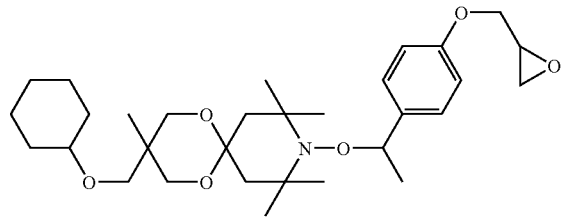

15.) 3-Benzyloxymethyl-3,8,8,10,10-pentamethyl-9-[1-(4-oxiranylmethoxy-phenyl)-ethoxy]-1,5-dioxa-9-aza-spiro[5.5]undecane

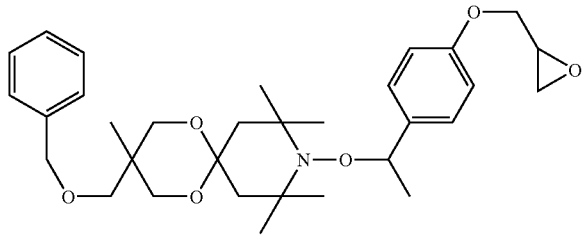

16.) Acetic acid 3,8,8,10,10-pentamethyl-9-[1-(4-oxiranylmethoxy-phenyl)-ethoxy]-1,5-dioxa-9-aza-spiro[5.5]undec-3-ylmethyl ester

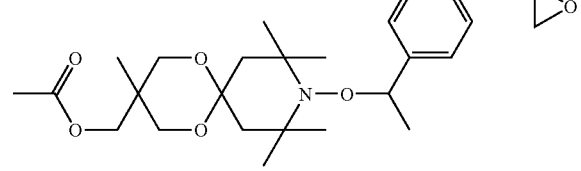

17.) 3,8,8,10,10-Pentamethyl-9-[1-(4-oxiranylmethoxy-phenyl)-ethoxy]-1,5-dioxa-9-aza-spiro[5.5]undecane-3-carboxylic acid methyl ester

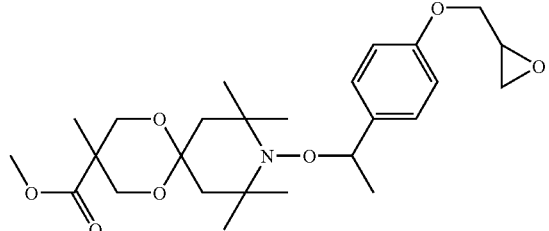

18.) 8,8,10,10-Tetramethyl-9-[1-(4-oxiranylmethoxy-phenyl)-ethoxy]-1,5-dioxa-9-aza-spiro[5.5]undecane-3,3-dicarboxylic acid diethyl ester

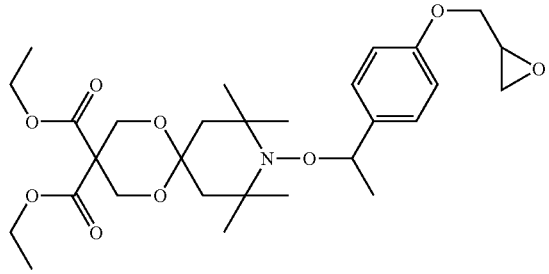

19.) 2,2,4,4-Tetramethyl-3-[1-(4-oxiranylmethoxy-phenyl)-ethoxy]-7,12-dioxa-3-aza-spiro[5.6]dodec-9-ene

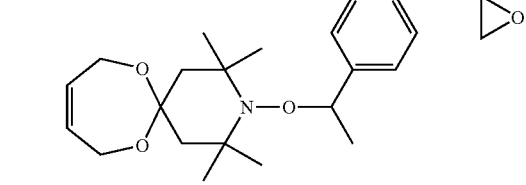

Examples of compounds IIb, wherein Z and Z' together form a tetravalent group are:
1.) Octanedioic acid bis-{7,7,9,9-tetramethyl-8-[1-(4-oxiranylmethoxy-phenyl)-ethoxy]-1,4-dioxa-8-aza-spiro[4.5]dec-2-ylmethyl}ester

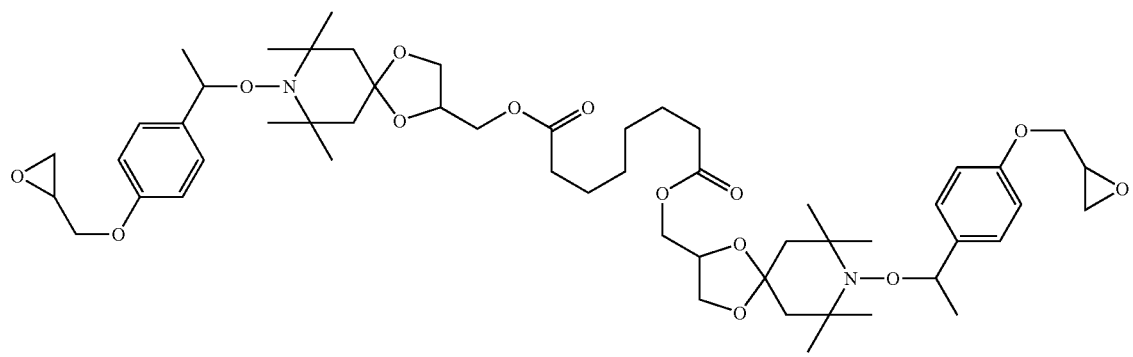

2.) Terephthalic acid bis-{7,7,9,9-tetramethyl-8-[1-(4-oxiranylmethoxy-phenyl)-ethoxy]-1,4-dioxa-8-aza-spiro[4.5]dec-2-ylmethyl}ester
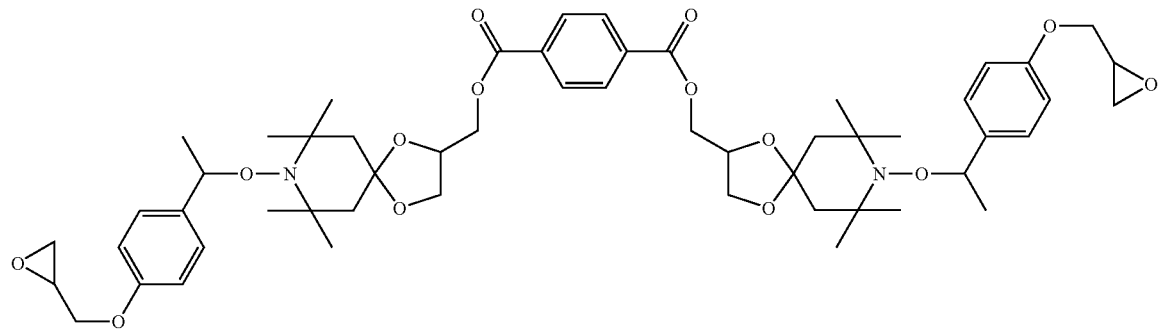
3.) 1',4'-Bis-{7,7,9,9-tetramethyl-8-[1-(4-oxiranylmethoxy-phenyl)-ethoxy]-1,4-dioxa-8-aza-spiro[4.5]dec-2-ylmethyl)-oxybutane
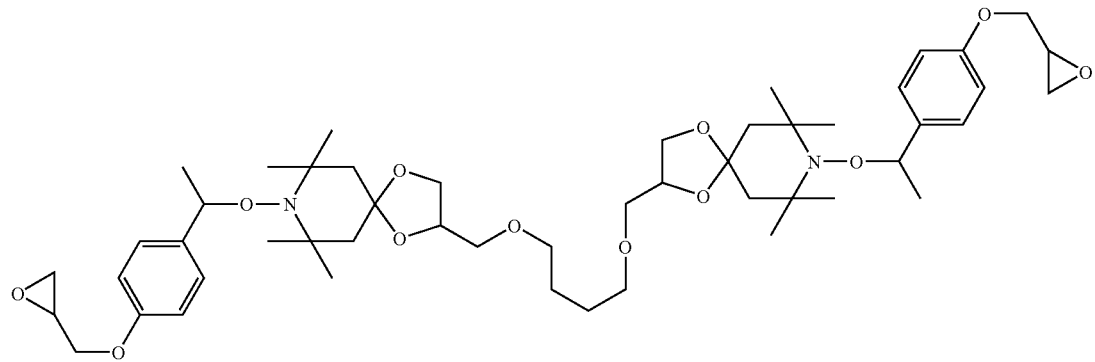
4.) Octanedioic acid bis-{3,8,8,10,10-pentamethyl-9-[1-(4-oxiranylmethoxy-phenyl)-ethoxy]-1,5-dioxa-9-aza-spiro[5.5]undec-3-ylmethyl}ester
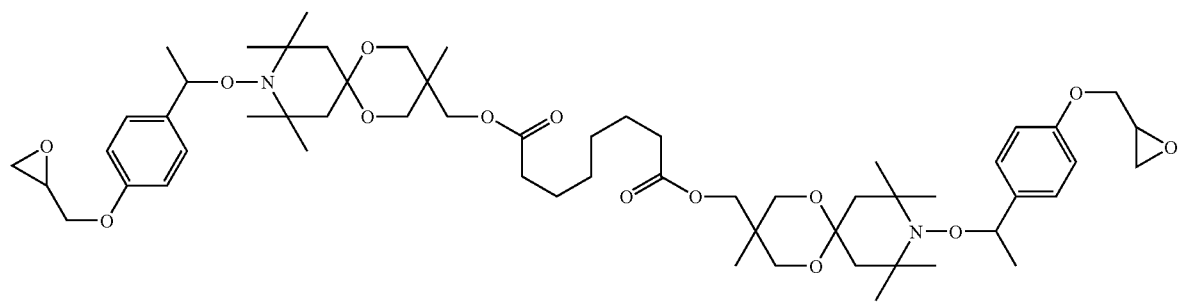

5.) 1',6'-Bis-{8,8,10,10-tetramethyl-9-[1-(4-oxiranyl-methoxy-phenyl)-ethoxy]-1,5-dioxa-9-aza-spiro[5.5]un-dec-3-ylmethyl}-oxyhexane

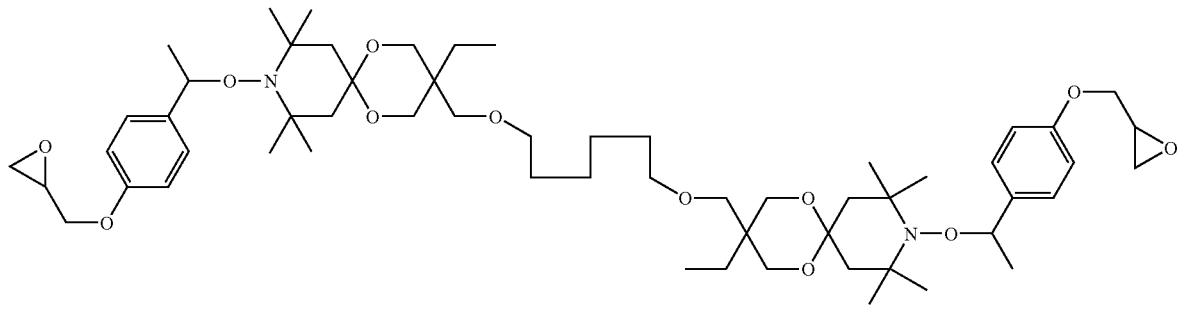

6.) 3,3-Bis-{8,8,10,10-tetramethyl-9-[1-(4-oxiranyl-methoxy-phenyl)-ethoxy]-1,5-dioxa-9-aza}-spiro[5.5]un-decane

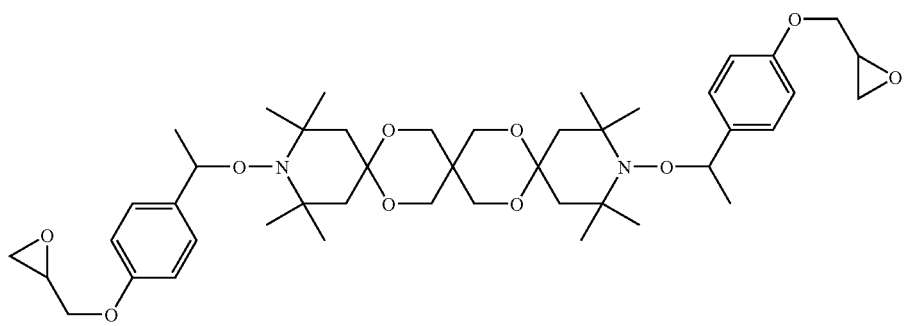

Further Examples of compounds II are:

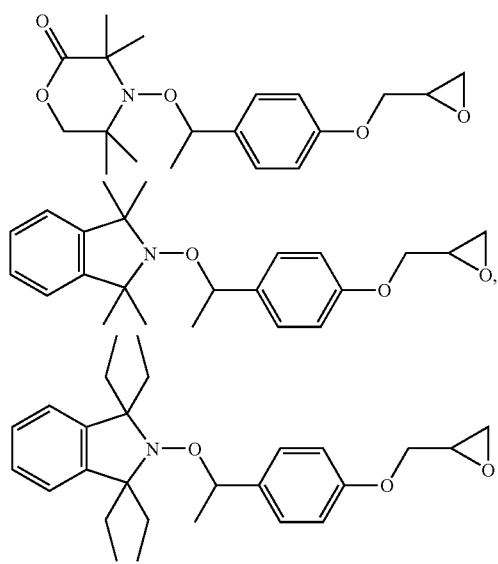

New Compounds

Compounds of the formula II, wherein D is a group —O—CH$_2$—CH(OH)—CH$_2$—NR$_{12}$R$_{13}$ or a group —O—CH$_2$—CH(OH)—CH$_2$—W—CH$_2$—CHOH—CH$_2$—O— with W being a divalent amino group (—N(R$_{12}$)—, a polyamine residue, a polyethyleneimine residue or a polyoxyalkyleneamine residue.

Preparation:

Compounds according to formula (I) or (II) may be prepared in different ways according to known methods. These methods are for example described in Macromol. Rapid Commun. 17, 149, 1996, Macromol Symp. 111, 47, (1996), Polym. Degr. Stab. 55, 323 (1997), Synlett 1996, 330, U.S. Pat. No. 5,498,679 or U.S. Pat. No. 4,921,962.

The starting compounds, which are phenylglycidylethers are known and either commercially available or may be prepared according to EP 226543.

Synthesis of compounds II, especially of compounds IIa, wherein D is a group

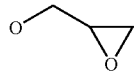

is described in WO 99/46261.

The preparation of the compounds of the formula IIb is carried out according to known reaction steps. A general method for the preparation is described in the Publication WO02/48109 (PCT Application PCT/EP/01/13071).

The preparation starts from the 4-oxo compound XIIa which is a known compound described for example in DE 2352127.

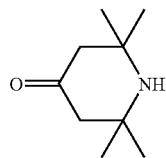
(XIIa)

The starting compound is reacted for example with suitable monoalcohols, diols or tetra-functional alcohols to form intermediates of formula XIIb. Such ketalization reactions are well known in the art and the corresponding compounds are mostly known. The reaction is for example described in U.S. Pat. Nos. 3,790,525, 3,899,464, 4,007,158 and 4,105,626.

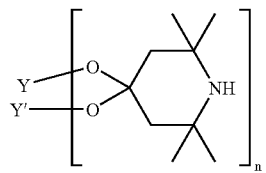
(XIIb)

The compound of formula XIIb is oxidized according to standard procedures to the corresponding nitroxide of formula XIIc, as for example described in WO 99/46261.

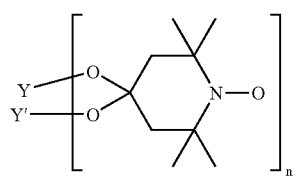
(XIIc)

The nitroxides are then reacted with a compound of formula

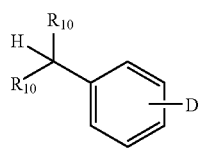

wherein $R_{10}$ is as defined above to obtain a compound of formula IIb.

This coupling reaction is also descriebed for example in GB 2335190 or in WO 99/46261.

The new compounds of formula II, wherein D is a group —O—CH$_2$—CH(OH)—CH$_2$—NR$_{12}$R$_{13}$ or a group —O—CH$_2$—CH(OH)—CH$_2$—W—CH$_2$—CHOH—CH$_2$—O— with W being a divalent amino group (—N(R$_{12}$)—, a polyamine residue, a polyethyleneimine residue or a polyoxyalkyleneamine residue may be prepared by reaction of a compound of the formula II wherein D is a group

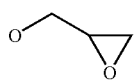

with a monoamine, a polyamine residue, a polyethyleneimine residue or a polyoxyalkyleneamine residue in a suitable solvent.

The choice of the solvent is not critical. Examples are alcohols, ethers, THF and the like.

Examples of monoamines are NH$_3$ or primary amines like NH$_2$-alkyl, NH$_2$-alkenyl, NH$_2$-alkinyl, NH$_2$-aralkyl, NH$_2$-cycloalkyl, NH$_2$-Aryl, or secundary amines like alkyl-NH-alkyl' and mixed combinations with alkyl, alkenyl, alkinyl, cycloalkyl, aralkyl, aryl.

Alkyl, alkenyl, alkinyl, cycloalkyl, aralkyl, aryl can be linear or branched or unsaturated, or can be interrupted by N, O, S or CO, SO, SO$_2$; it can be further substituted by alkyl, OH, Oalkyl, Oaryl, Oaralkyl, COOH, COOalkyl, amidgroups or halogene;

Use

Compounds according to the invention are preferably used in the dye providing light-sensitive layers, in a quantity of 0.1 to 2 mol/mol of color coupler, in particular in a quantity of 0.1 to 0.5 mol/mol of color coupler.

Compounds according to the present invention are most preferably used in yellow dye providing blue-sensitive layers.

Compounds of the formula II, wherein D is a group —O—CH$_2$—CH(OH)—CH$_2$—NR$_{12}$R$_{13}$ or a group —O—CH$_2$—CH(OH)—CH$_2$—W—CH$_2$—CHOH—CH$_2$—O— with W being a divalent amino group (—N(R$_{12}$)—, a polyamine residue, a polyethyleneimine residue or a polyoxyalkyleneamine residue can be used also for the controlled free radical polymerization of ethylenically unsaturated monomers.

Yellow couplers that can be used in combination with the dye stabilisers according to the invention are preferably compounds of the formula A:

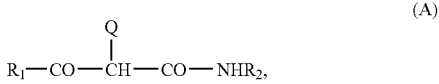
(A)

wherein $R_1$ is alkyl, cycloalkyl, arylamino, anilino, a heterocyclic group or aryl, $R_2$ is aryl and Q is hydrogen or a group which can be eliminated by reaction with the oxidised developer.

One particularly preferred group of yellow couplers are those compounds of formula A, wherein $R_1$ is t-butyl and $R_2$ is a group of formula

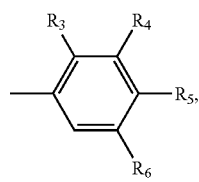

wherein $R_3$ is hydrogen, halogen, alkyl or alkoxy, and $R_4$, $R_5$ and $R_6$ are hydrogen, halogen, alkyl, alkenyl, alkoxy, aryl, carboxy, alkoxycarbonyl, a carbamoyl group, a sulfonic or sulfamoyl group, an alkylsulfonamino group, acylamino group, ureido group or amino group. $R_3$ is preferably chloro or methoxy, $R_4$ and $R_5$ are preferably hydrogen, and $R_6$ is preferably an acylamino group. This includes also the compounds of formula

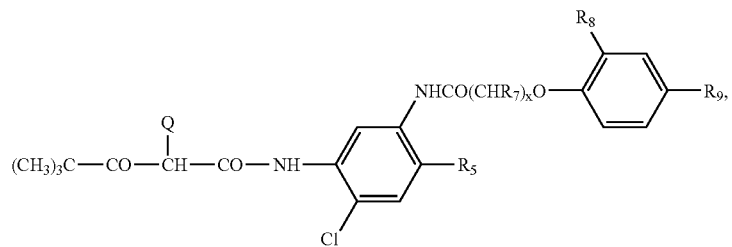

wherein x is a number 0–4, $R_7$ is hydrogen or alkyl, and $R_8$ and $R_9$ are alkyl.

Another group of yellow couplers that can be used in combination with the dye stabilisers according to the invention conforms to formula B:

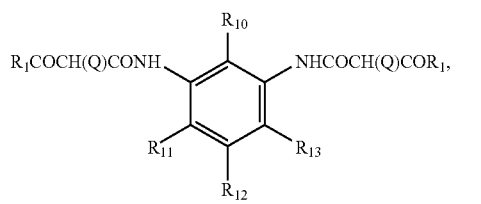

wherein $R_{10}$ is hydrogen, halogen or alkoxy,
$R_{11}$, $R_{12}$ and $R_{13}$ are hydrogen, halogen, alkyl, alkenyl, alkoxy, aryl, carboxyl, alkoxycarbonyl, a carbamoyl group, a sulfonic group, sulfamoyl group, sulfonamido group, acylamino group, ureido group or amino group, and $R_1$ and Q have the meaning cited above.

These couplers include compounds of formula B, in which $R_1$ is t-butyl, $R_{10}$ is chloro, $R_1$, and $R_{13}$ are hydrogen, and $R_{12}$ is alkoxycarbonyl.

In the compounds of formula A and B, the group Q may be hydrogen (4-equivalent coupler) or a heterocyclic group (2-equivalent coupler)

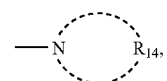

wherein $R_{14}$ is an organic divalent group which makes the ring up into a 4–7-membered ring, or Q is a group —$OR_{15}$, wherein $R_{15}$ is alkyl, aryl, acyl or a heterocyclic radical.

Typical examples of customary yellow couplers are the compounds of the following formulae (I to IV):

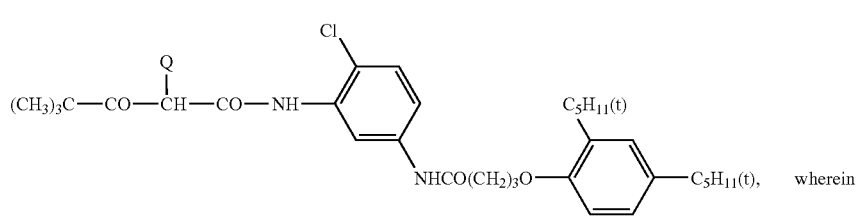

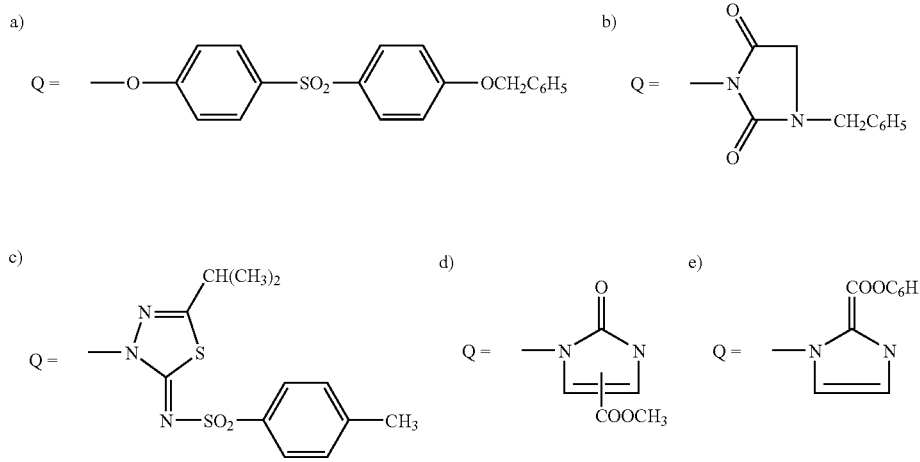

-continued
i) 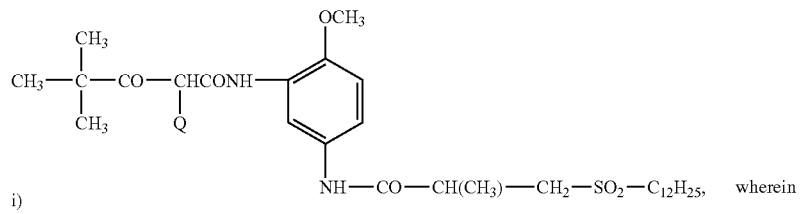
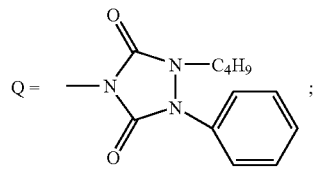
f) 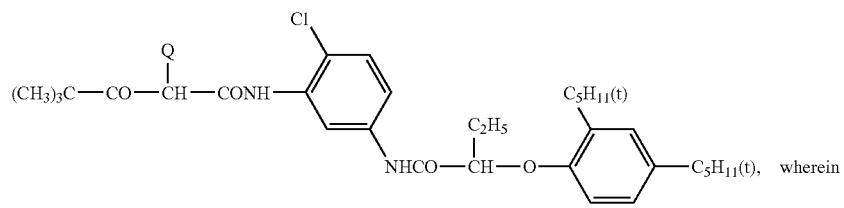
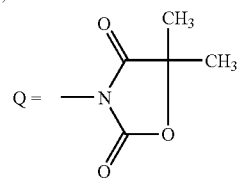 g) 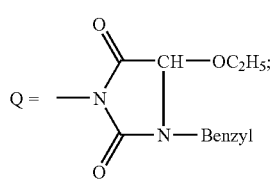
h) 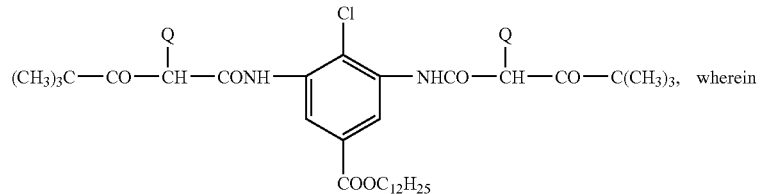
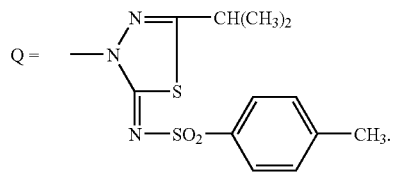
Particularly suited yellow couplers conform to formulae (Y-1) to (Y-19):
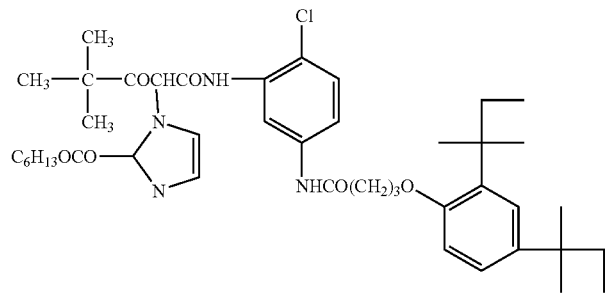
(Y-1)

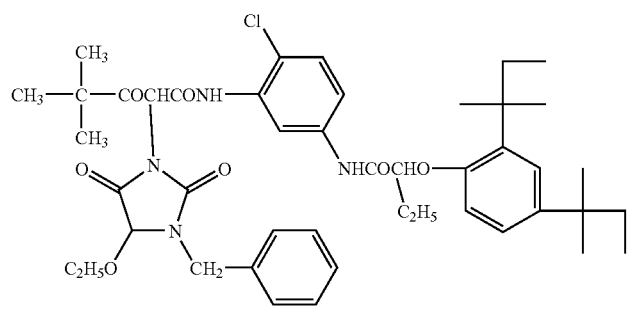
(Y-2)
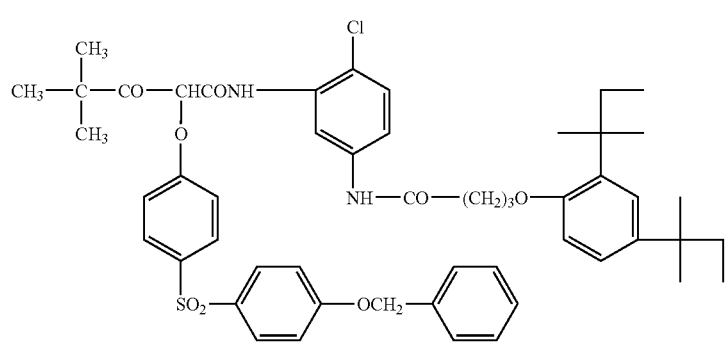
(Y-3)
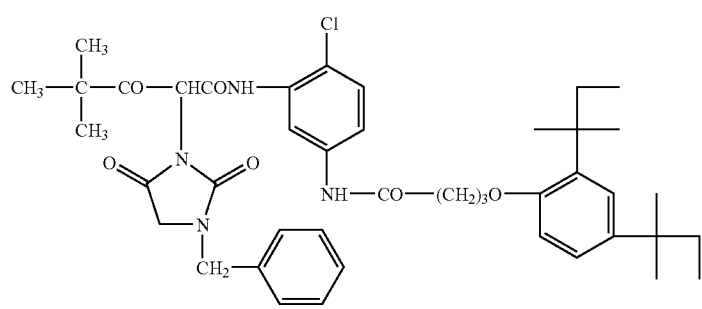
(Y-4)
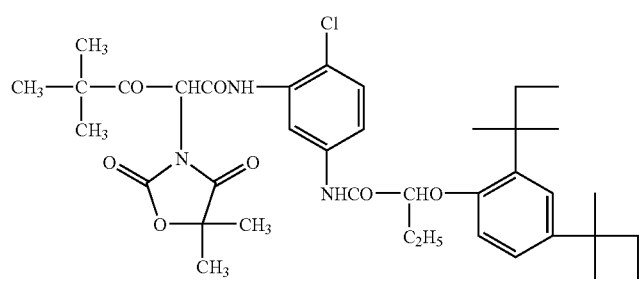
(Y-5)
wherein ⊥ = —C(CH₃)₂C₂H₅ = —C₅H₁₁(t);

-continued
(Y-6)
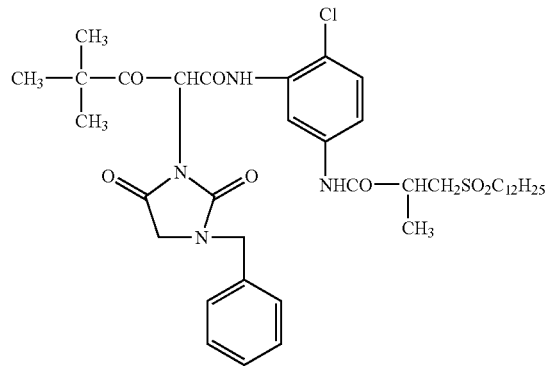
(Y-7)
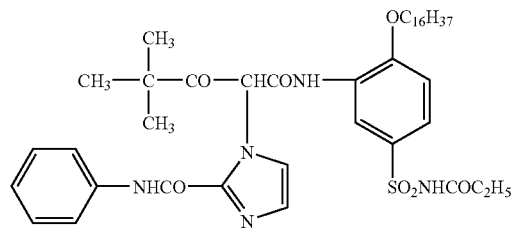
(Y-8)
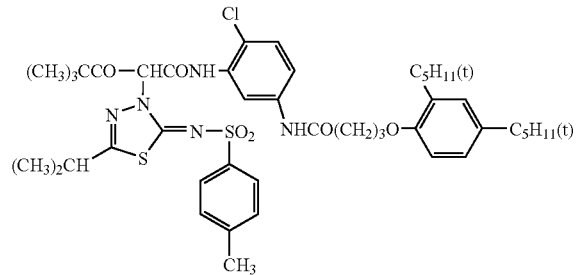
(Y-9)
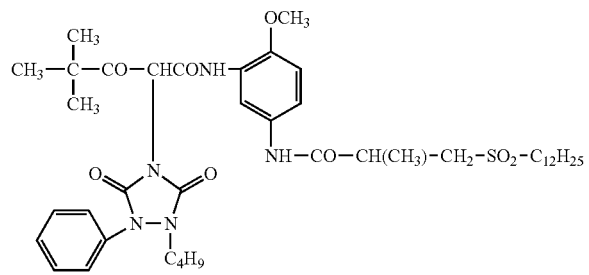
(Y-10)
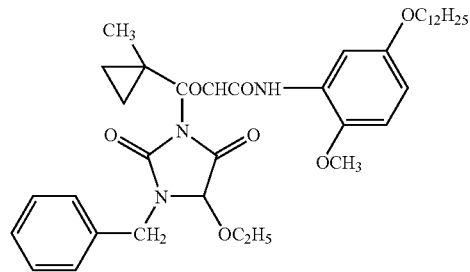

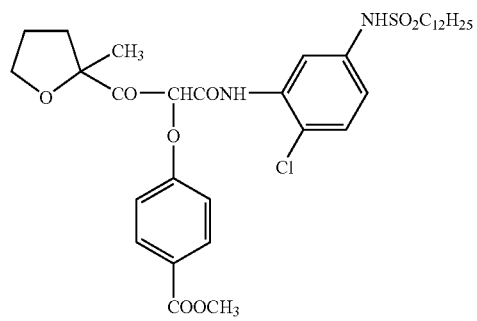
(Y-11)
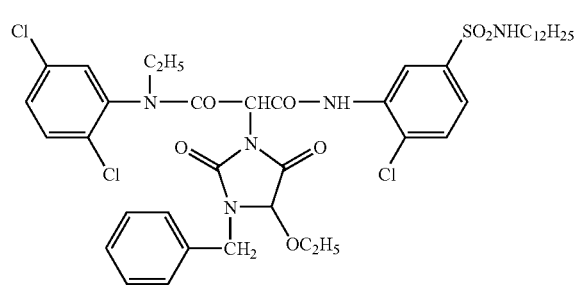
(Y-12)
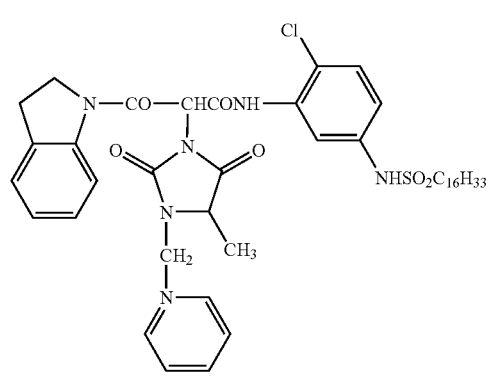
(Y-13)
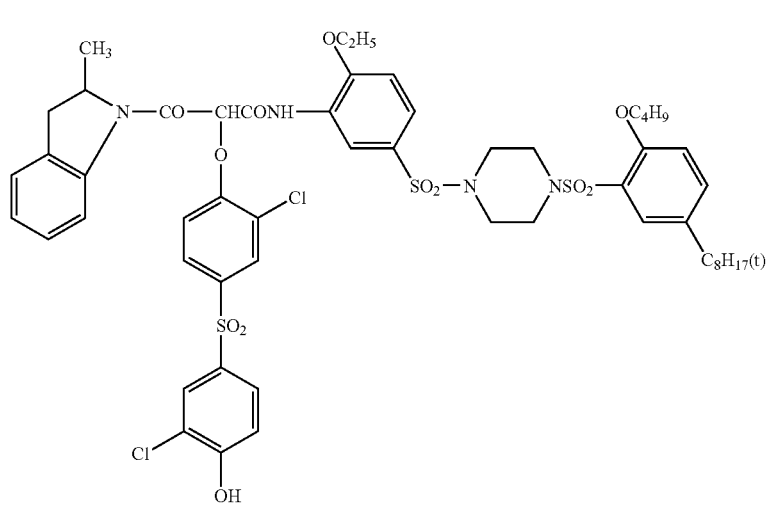
(Y-14)

(Y-15)
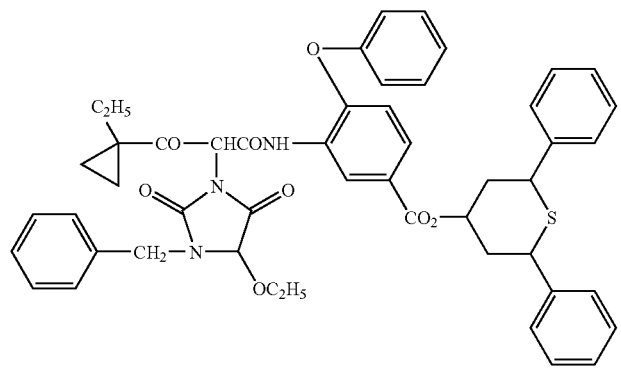
(Y-16)
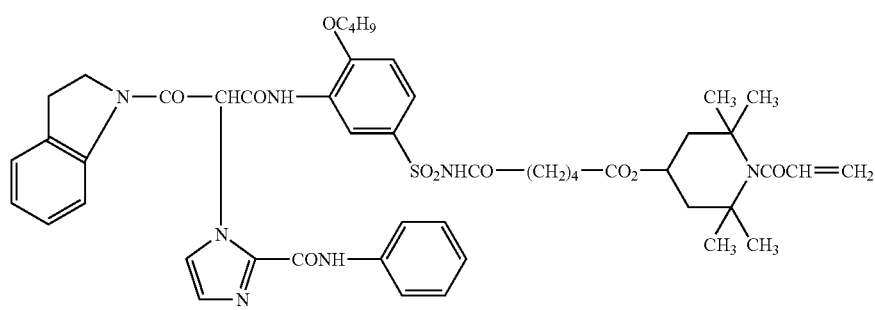
(Y-17)
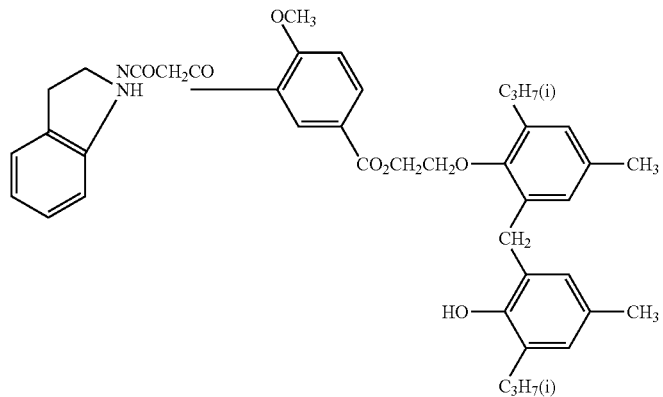
(Y-18)
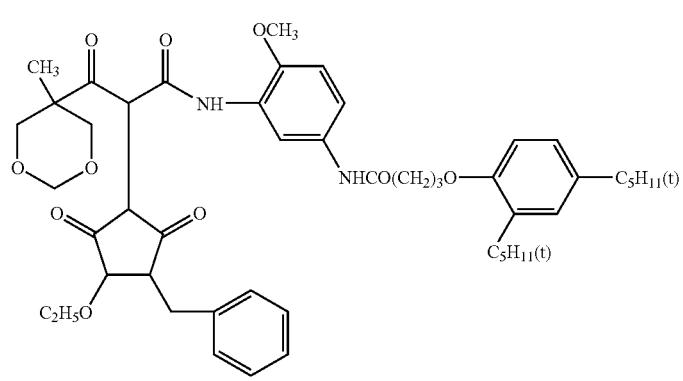

-continued (Y-19)

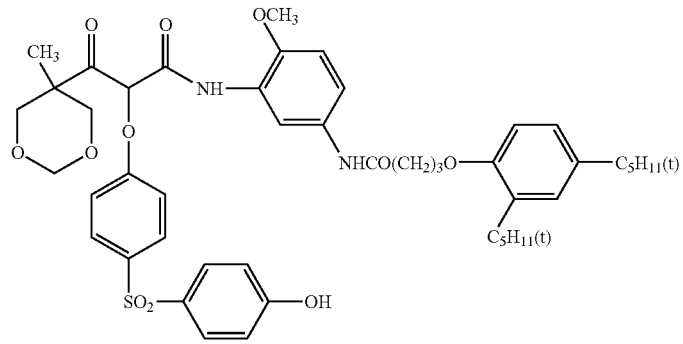

Further examples of suited yellow couplers are to be found in U.S. Pat. Nos. 2,407,210, 2,778,658, 2,875,057, 2,908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, 4,540,657, 5,001,045, 5,118,599, 5,183,731, 5,215,878, 5,260,182, 5,294,527, 5,298,375, 5,298,383, 5,300,412, 5,306,609, 5,314,797, 5,316,903, 5,336,591, 5,455,149, 5,441,855, 5,466,569, 5,521,058, in DE-A 1,547,868, 2,057,941, 2,162,899, 2,163,813, 2,213, 461, 2,219,917, 2,261,361, 2,261,362, 2,263,875, 2,329,587, 2,414,006 and 2,422,812; in GB-A 1,425,020 and 1,077,874, and in JP-A-88/123,047, U.S. Pat. Nos. 4,133,052, 5,080, 469, 5,313,323; in JP-A 08-286338, -234381, -160578, -160577, -160576, and in EP-A-447,969, 447,920, 508,398, 510,535, 542,463, 568,198, 710,882, 751,428 and EP-B-482,552.

The yellow couplers are customarily used in an amount of 0.05–2 mol, preferably of 0.1–1 mol, per mol of silver halide.

Examples of colour photographic materials according to this invention are colour negative films, colour reversal films, colour positive films, colour photographic paper, colour reversal photographic paper, colour-sensitive materials for the dye diffusion transfer process or the silver dye bleach process.

Typical bases for silver halide photographic materials include polymeric films and polymer-coated paper. Details regarding supports for colour photographic recording materials can be found in Research Disclosure, Item 36544, September 1994.

Examples of suitable bases for the production of colour photographic materials are films and sheets of semisynthetic and synthetic polymers, such as cellulose nitrate, cellulose acetate, cellulose butyrate, polystyrene, polyvinyl chloride, polyethylene terephthalate, polyalkylene naphthalate (e.g. as disclosed in U.S. Pat. No. 5,824,465) and polycarbonate, and paper laminated with a barytes layer or an α-olefin polymer layer (e.g. polyethylene). These bases can have been coloured with dyes or pigments, for example titanium dioxide. They can also have been coloured black for the purposes of light shielding. The surface of the base is generally subjected to a treatment for improving the adhesion of the photographic emulsion layer, for example corona discharge with subsequent application of a substrate layer.

Essential constituents of the colour-photographic emulsion layers are binders, silver halide particles and colour couplers. Details regarding the constituents of light sensitive layers and other (non light sensitive) layers such as top layers and interlayers separating the silver halide emulsion layers can be found in Research Disclosure, Item 38957, September 1996.

The binder used is preferably gelatin. However, gelatin may be replaced entirely or in part by other synthetic, semisynthetic or naturally occurring polymers. Synthetic gelatin substitutes are, for example, polyvinyl alcohol, poly-N-vinylpyrrolidone, polyacrylamide, polyacrylic acid or their derivatives, in particular their copolymers. Naturally occurring gelatin substitutes are, for example, other proteins such as albumin or casein, cellulose, sugar, starch or alginates. Semisynthetic gelatin substitutes are as a rule modified natural products. Examples thereof are cellulose derivatives, such as hydroxyalkylcellulose, and gelatin derivatives, which are obtained by reaction with alkylating or acylating agents or by being grafted with polymerisable monomers.

The binders should contain a sufficient amount of functional groups so that it is possible to produce sufficiently resistant layer by reaction with suitable hardeners. Such functional groups are, in particular, amino groups and also carboxyl groups, hydroxyl groups and active methylene groups.

The halide in the silver halide present in the photographic material as photosensitive component can contain chloride, bromide or iodide, or mixtures thereof. The halide in at least one layer can, for example, consist to 0 to 15 mol % of iodide, to 0 to 100 mol % of chloride and to 0 to 100 mol % of bromide. In the case of colour negative and colour reversal films, it is usual to use silver bromide iodide emulsions, in the case of colour negative and colour reversal papers silver chloride bromide emulsions having a high chloride content, for example at least 90 mol % silver chloride up to pure silver chloride emulsions. They may be predominantly compact crystals which are e.g. regularly cubic or octaedric or which can have transition forms. Preferably, however, it is also possible to use platy crystals having an average ratio of diameter to thickness of preferably at least 5:1, the diameter of a grain being defined as the diameter of a circle having a circular area corresponding to the projected area of the grain. The layers can, however, also contain platy silver halide crystals having a ratio of diameter to thickness which is substantially higher than 5:1, for example from 12:1 to 30:1.

The silver halide grains may also have a multi-layered grain structure, in the simplest instance having an inner and outer grain area (core/shell), the halide composition and/or other modifications, e.g. dopings of the individual grain areas, being different. The average grain size of the emulsions is preferably in the range of 0.2 mm to 2.0 mm, and the grain size distribution can be both homo- and heterodisperse. Homodisperse grain size distribution means that 95% of the grains do not deviate more than ±30% from the average grain size. Besides the silver halide, the emulsions can also contain organic silver salts, for example silver benzotriazolate or silver behenate.

Two or more kinds of silver halide emulsions, prepared separately, may be used as a mixture.

The photographic emulsions can be prepared from soluble silver salts and soluble halides by different methods (e.g. P. Glafkides, Chimie et Physique Photographiques, CEP Editions, Paris (1987), G. F. Duffin, Photographic Emulsion Chemistry, The Focal Press, London (1966), V. L. Zelikman et al, Making and Coating Photographic Emulsion, The Focal Press, London (1966)).

The silver halide emulsions are usually subjected to a chemical sensitization under defined conditions—pH, pAg, temperature, the concentration of gelatin, silver halide and sensitiser—until optimum sensitivity and fogging is reached. The process is described, inter alia, in H. Frieser "Die Grundlagen der Photographischen Prozesse mit Silverhalogeniden" p. 675–734, Akademische Verlagsgesellschaft (1968).

The chemical sensitization can be carried out with addition of sulfur, selenium, tellurium compounds and/or compounds of the metals of the VIIIth side group of the periodic system (e.g. gold, platinum, palladium, iridium). It is also possible to add thiocyanate compounds, surfactants, such as thioethers, heterocyclic nitrogen compounds (e.g. imidazoles, azaindenes) or also spectral sensitisers (described, inter alia, in F. Hamer "The Cyanine Dyes and Related Compounds", 1964, or in Ullmanns Encyclopadie der technischen Chemie, $4^{th}$ edition, Vol. 18, p. 431 ff, and in Research Disclosure 17643 (December 1978), chapter III. Instead or additionally, it is possible to carry out a reduction sensibilisation with addition of reduction agents (tin-II-salts, amines, hydrazine derivatives, aminoboranes, silanes, formamidinesulfinic acid) by means of hydrogen, low pAg (e.g. lower than 5) and/or high pH (e.g. above 8).

The photographic emulsions might contain compounds for preventing fogging or for stabilising the photographic function during production, storage or photographic processing.

Azaindenes are particularly suitable, preferably tetra- and pentaazaindenes, more preferably those which are substituted by hydroxyl groups or amino groups. Such compounds have been described, for example, by Birr, Z. Wiss. Phot. 47 (1952), p. 2–58. Antifogging agents used may be, for example, salts of metals, such as of mercury or cadmium, aromatic sulfonic or sulfinic acids, such as benzenesulfinic acid, or nitrogen-containing heterocycles, such as nitrobenzimidazole, nitroindazole, unsubstituted or substituted benzotriazoles or benzothiazolium salts. Mercapto group-containing heterocycles are particularly suitable, e.g. mercaptobenzothiazoles, mercaptobenzimidazoles, mercaptotetrazoles, mercaptothiadiazoles, mercaptopyrimidines, which mercaptoazoles can also contain a water-solubilising group, for example a carboxyl group or sulfo group. Other suitable compounds are published in Research Disclosure 17643 (December 1978).

The stabilisers can be added to the silver halide emulsions before, during or after their ripening. It is also possible to add the compounds also to other photographic layers allocated to a silver halide layer.

It is also possible to use mixtures of two or more of the cited compounds.

The photographic emulsion layers or other hydrophilic colloid layers of the photosensitive material prepared according to this invention can contain surfactants for different purposes, such as coating aids, agents for preventing electrical charging, lubricants, agents for emulsifying the dispersion, agents for preventing adhesion and agents for improving the photographic characteristics (e.g. development accelerators, high contrast, sensibilisation etc.). Besides natural surfactants, e.g. saponin, synthetic surfactants are mainly used; non-ionic surfactants, e.g. alkylene oxide compounds, glycerin compounds or glycidol-compounds, cationic surfactants, e.g. higher alkylamines, quarternary ammonium salts, pyridine compounds and other heterocyclic compounds, sulfonium compounds or phosphonium compounds, anionic surfactants containing an acid group, e.g. a carboxylic acid, sulfonic acid, phosphoric acid, a sulfate or phosphate group, ampholytic surfactants, e.g. amino acid and aminosulfonic acid compounds, and also sulfates or phosphates of an amino alcohol.

The photographic emulsions are usually spectrally sensitised using methine dyes or other dyes. Particularly suitable dyes are cyanine dyes, merocyanine dyes and complex merocyanine dyes.

Research Disclosure 17643 (December 1978), provides an overview of the polymethine dyes suitable as spectral sensitisers, of their suitable combinations and of combinations which act as supersensitisers.

Particularly suitable dyes are the following dyes, listed according to their spectral ranges:

1. As Red Sensitisers 9-ethylcarbocyanine containing benzothiazole, benzoselenazole or naphthothiazole as basic end groups which may be substituted in 5- and/or 6-position by halogen, methyl, methoxy, carbalkoxy, aryl, as well as 9-ethyl-naphthoxathia- or -selencarbocyanines and 9-ethylnaphthothiazoxa- or -benzimidazocarbocyanines, provided the dyes carry at least one sulfoalkyl group at the heterocyclic nitrogen.

2. As Green Sensitisers 9-ethylcarbocyanines containing benzoxazole, naphthoxazole or a benzoxazole and a benzothiazole as basic end groups and also benzimidazocarbocyanines, which can likewise be further substituted and which also contain at least one sulfoalkyl group at the heterocyclic nitrogen.

3. As Blue Sensitisers symmetrical or asymmetrical benzimidazo-, oxa-, thia- or selenacyanines containing at least one sulfoalkyl group at the heterocyclic nitrogen and, optionally, additional substituents at the aromatic nucleus, and apomerocyanines containing a rhodanine group.

It is possible to forego the use of sensitisers if the inherent sensitivity of the silver halide, for example the blue sensitivity of silver bromides, is sufficient for a specific spectral range.

To the differently sensitised emulsion layers are allocated non-diffusing monomeric or polymeric colour couplers, which may be located in the same layer or in an adjacent layer. It is common to assign cyan couplers to the red-sensitive layers, magenta couplers to the green-sensitive layers and yellow couplers to the blue-sensitive layers.

Cyan couplers are typically of the phenol, naphtol or pyrazoloazole type.

Magenta couplers are, for example, simple 1-aryl-5-pyrazolones, or pyrazole derivatives condensed with 5-membered hetero rings, such as imidazopyrazoles, pyrazolopyrazoles, pyrazolotriazoles or pyrazolotetrazoles.

Examples of magenta and cyan couplers that can be used in a photographic material according to the present invention can be found in GB A 2 343 007, which is included herein as reference, as well as in references cited therein.

Yellow couplers are generally couplers with an open chain ketomethylene group, in particular couplers of the α-acylacetamide type. Suitable examples of yellow couplers are given above.

Colour couplers might be 4-equivalent or 2-equivalent couplers. The latter are differentiated from 4-equivalent couplers by containing a substituent at the coupling position, which is eliminated upon coupling with colour developer oxidation products.

The couplers customarily contain a ballast residue in order to prevent intra- and interlayer wandering. High molecular weight couplers might be used instead and are described, inter alia, in DE-A-1297417, DE-A-2407569, DE-A-3148125, DE-A-3217200, DE-A-3320079, DE-A-3324932, DE-A-3331743, DE-A-3340376, EP-A-27284, U.S. Pat. No. 4,080,211. The high molecular weight colour couplers are usually prepared by polymerisation of ethylenically unsaturated monomeric colour couplers. However, they can also be obtained by polyaddition or polycondensation.

The incorporation of the couplers or other compounds, including the stabilizers according to this invention, in a silver halide emulsion layer can be carried out such that a solution, dispersion or emulsion is prepared from the respective compound, which is then added to the casting solution used for the layer in question. Selection of the appropriate solvent or dispersant depends on the particular solubility of the compound.

Methods for the incorporation of compounds which are essentially immiscible in water by grinding processes are described, inter alia, in DE-A-2609741, DE-A-2609742 and in EP-A-694590. The grinding process can be complemented by a thermal process by heating the emulsion to above the melting point of the compounds to be dispersed, with rapid subsequent cooling (EP-B-515674). Dispersants for the stabilisation of dispersions of solid particles are described, inter alia, in U.S. Pat. No. 5,591,568.

Hydrophobic compounds can also be incorporated in the casting solutions using high-boiling solvents, so-called oil formers. Corresponding methods are described, inter alia, in U.S. Pat. Nos. 2,322,027, 2,801,170, 2,801,171 and EP-A-0043037.

The high-boiling solvents can be replaced with oligomers or polymers, so-called polymeric oil formers.

The compounds can also be incorporated in the casting solution in the form of loaded latices, see for example DE-A-2541230, DE-A-2541274, DE-A-2835856, DE-A-19536376, EP-A-0014921, EP-A-0069671, EP-A-0130115, U.S. Pat. No. 4,291,113.

The diffusion-stable incorporation of anionic water-soluble compounds (e.g. of dyes) can also be carried out by means of cationic polymers, so-called mordant polymers.

The compounds according to this invention can be incorporated singly or together with the colour coupler and, optionally, other additives in the colour photographic material by predissolving them in high-boiling organic solvents.

Suitable high-boiling solvents are, for example, alkyl phthalates, phosphonates, phosphorates, citrates, benzoates, amides, fatty acid esters, trimesinates, alcohols, phenols, aniline-derivatives and hydrocarbons.

Examples of suitable high-boiling solvents are dibutylphthalate, dicyclohexylphthalate, di-2-ethylhexylphthalate, decylphthalate, triphenylphosphate, tricresylphosphate, 2-ethylhexyldiphenylphosphate, tridecylphosphate, tributoxyethylphosphate, trichloropropylphosphate, di-2-ethylhexylphenylphosphate, 2-ethylhexylbenzoate, dodecylbenzoate, 2-ethylhexyl-p-hydroxybenzoate, diethyldodecanamide, N-tetradecylpyrrolidone, isostearyl alcohol, 2,4-di-t—amylphenol, dioctylacelate, glycerol tributyrate, isostearyllactate, trioctylcitrate, N,N-dibutyl-2-butoxy-5-t-octylaniline, paraffin, didecylbenzene and diisopropylnaphthalene.

The amount of high-boiling solvent used is in the range of, for example, 50 mg to 2 g per $m^2$ support, preferably of 200 mg to 1 g per $m^2$.

A low-boiling solvent might be used in addition to the oil former, in order to simplify incorporation of hydrophobic compounds into the colour-photographic recording material.

Examples of such solvents are esters, for example ethyl acetate, alcohols, for example butanol, ketones, for example methyl isobutyl ketone, chlorinated hydrocarbons, such as methylene chloride, and amides, such as dimethylformamide. Where the compounds themselves are liquid, they can also be incorporated into the photographic material without the assistance of oil formers.

The photographic layers in the material of this invention may also-include UV absorbers, which screen out the UV light and therefore protect the dyes, the couplers or other components against photodegradation.

Preferred UV absorbers to be used in a photographic material according to the present invention include benzotriazoles, 2-hydroxybenzophenrones, oxanilides, cyanoacrylates, salicylic esters, acrylonitrile derivatives, thiazolines and 2-hydroxyphenyltriazines.

Such UV absorbers are described in more detail, for example, in the following publications: U.S. Pat. Nos. 3,314,794, 3,352,681, 3,705,805, 3,707,375, 4,045,229, 3,700,455, 3,700,458, 3,533,794, 3,698,907, 3,705,805, 3,738,837, 3,762,272, 4,163,671, 4,195,999, 4,309,500, 4,431,726, 4,443,543, 4,576,908, 4,749,643,5500332, 5455152, GB-A-1,564,089, GB-A-2,293,608, EP-A-190, 003, -747755, -717313 and JP-A-71/2784, 81/111,826, 81/27,146, 88/53,543, 88/55,542 and 96/69087; and U.S. Pat. Nos. 5,300,414, 5,489,503, 5,480,108, 4,826,978, EP-A-706083, JP-A-08-267915, U.S. Pat. No. 5,364,749, WO 96/28431, GB-A-2319523. Particularly preferred UV absorbers are listed in GB-A-2343007.

The amount of the UV absorber or absorbers added is judiciously in the range from 0.001 to 10 g per $m^2$, for example from 0.1 to 8 $g/m^2$, especially from 0.005 to 6 and, in particular, from 0.01 to 4 $g/m^2$.

The photographic material can furthermore contain fluorescent whitening agents, spacers, filter dyes, formalin scavengers, light stabilisers, antioxidants, $D_{min}$ dyes, additives for improving the stability of dyes, couplers and whites and for reducing color stain, plasticisers (latices), biocides and other materials.

The non-photosensitive interlayers, which are usually arranged between light sensitive layers of different spectral sensitivity, usually contain so-called oxidised developer scavengers, i.e. compounds that prevent wandering of oxidised developer molecules from one silver halide emulsion layer to another one of different spectral sensitivity. Examples of suited oxidised developer scavengers can be found in Research Disclosure 17643 (December 1978), 17842 (February 1979) and 18716 (November 1979), and in EP-A-0069070, 0098072, 0124877, 0125522, 871066 and GB-A-2343007; these include hydrazine, hydrazide, hydroquinone, 6-hydroxychroman, hydroxylamine and lactone derivatives. Particularly suited oxidised developer scavengers for use in a photographic material according to this invention consist of the following compounds:

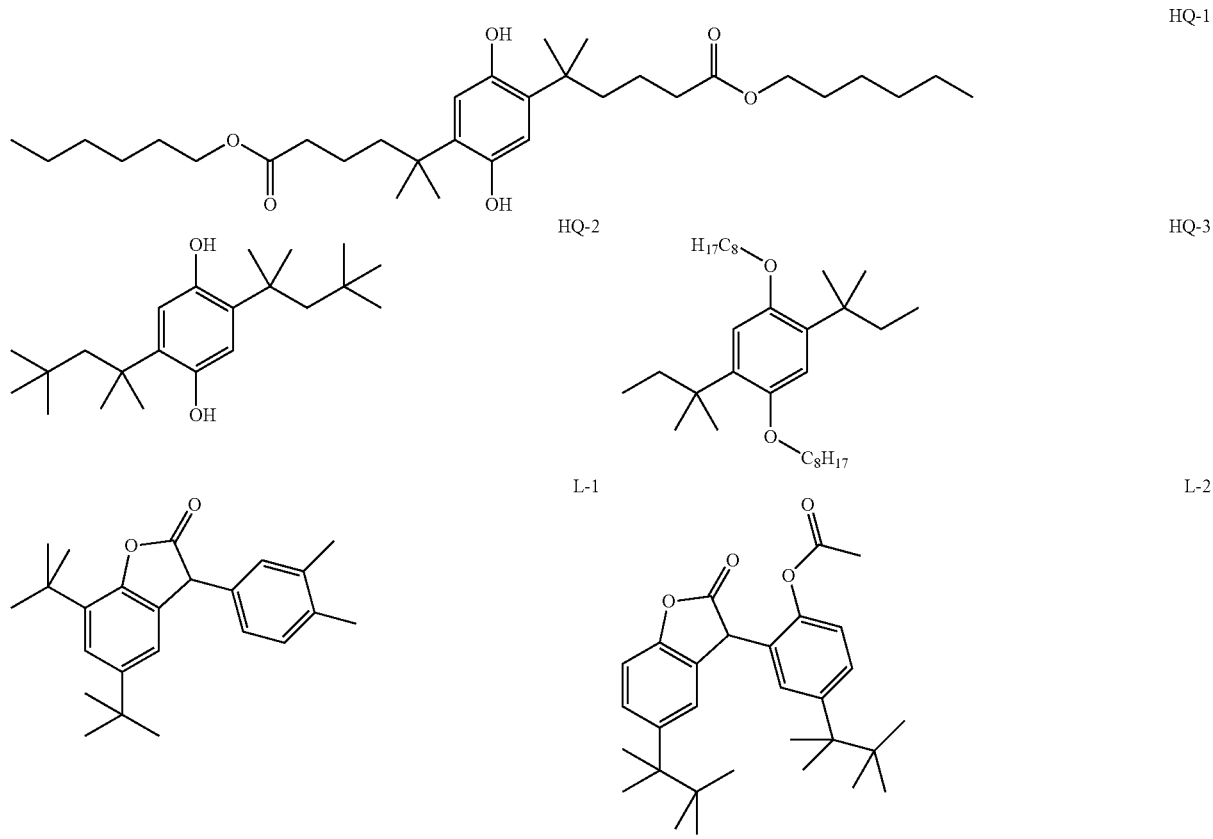

Filter dyes suitable for visible light include oxonol dyes, hemioxonol dyes, styryl dyes, merocyanine dyes, cyanine dyes and azo dyes. Of these, oxonol dyes, hemioxonol dyes and merocyanine dyes are particularly advantageous to use.

Suitable fluorescent whitening agents are described, inter alia, in Research Disclosure 17 643 (December 1978), chapter V, in U.S. Pat. Nos. 2,632,701, 3,269,840 and in GB-A-852075 and 1319763.

Certain binder layers, in particular the layer farthest away from the support, but in some cases also an interlayer, especially if it is the layer farthest away from the support during preparation, can contain photographically inert particles of inorganic or organic nature, for example as matting agents or as spacers (DE-A-3331542; DE-A-3424893, Research Disclosure 17 643 (December 1978), chapter XVI).

The average particle diameter of the spacers is preferably in the range of 0.2 to 10 mm. The spacers are water-insoluble and may be alkali-insoluble or alkali-soluble, those which are soluble in alkali usually being removed from the photographic material in the alkaline developer bath. Examples of suitable polymers are polymethylacrylate, copolymers of acrylic acid and methylmethacrylate as well as hydroxypropylmethylcellulose-hexahydrophthalate.

Suitable formalin scavengers are for example:

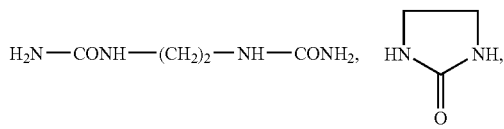

-continued

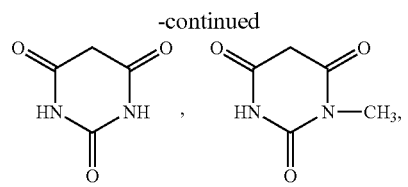

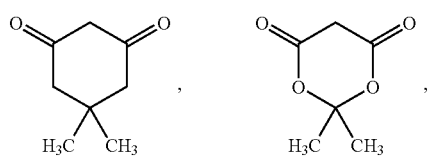

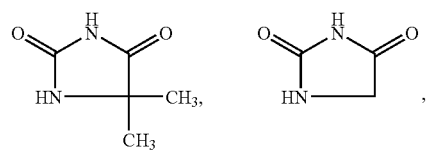

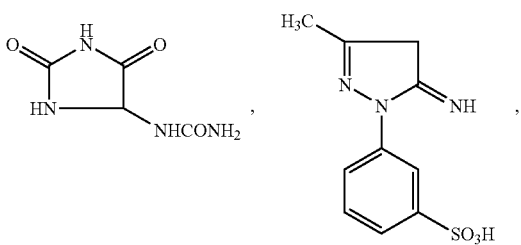

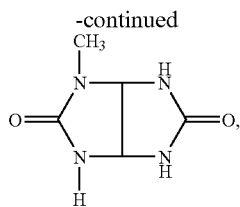

The photographic material according to this invention might also contain substances of formula

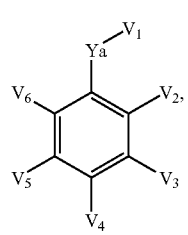

(A')

wherein Ya is —O—, —S— or —N(V$_7$)—;
V$_1$, V$_7$ are each independently of the other hydrogen, alkyl, aryl, acyl or a heterocycle, for example methyl, i-propyl, benzyl, hexadecyl, cyclohexyl, 2-phenoxyethyl, 2-methanesulfonamidoethyl, tetrahydropyranyl, morpholinyl. All cited radicals (except H and halogen) may be further substituted.
V$_2$–V$_6$ are each independently of one another hydrogen, Ya'—R$_1$', halogen, alkyl, aryl, acyl, acylamino, alkoxycarbonyl, aryloxycarbonyl, sulfonyl, carbamoyl, sulfamoyl; Ya' has the same meaning as Ya, and R$_1$' has the same meaning as R. All radicals (except H and halogen) may be further substituted. R$_2$–R$_6$ are, for example, methyl, fluoro, chloro, bromo, t-octyl, benzyl, cyclohexyl, n-dodecyl, s-butyl, 1,1-dimethyl-4-methoxycarbonylbutyl, acetyl, pivyloyl, dodecanoyl, benzoyl, 3-hexadecycloxybenzoyl, acetamino, pivaloylamino, 2-ethylhexyanoylamino, 2-(2,4-di-t-amylphenoxy)octanoylamino, dodecanoylamino, methoxycarbonyl, dodecyloxycarbonyl, 2,4-di-t-amylphenoxycarbonyl, 4-methoxyphenoxycarbonyl, methanesulfonyl, 4-dodecyloxybenzenesulfonyl, methylcarbamoyl, diethylcarbamoyl, N-methyl-N-phenylcarbamoyl.

Preferably, at least one of the V$_2$–V$_6$ substituents is Ya'—R$_1$'.

In addition, all the groups in ortho-position to one another in formula A' may make up a 5–8-membered ring (for example coumaran, chroman, indane, quinoline). These rings can further combine to form a bicyclic ring or a spiroring.

V$_1$ and V$_7$ can make up a 5–7-membered, preferably a saturated ring (e.g. piperazine, morpholine or the like). The rings obtained can be further substituted.

Such compounds are described, inter alia, in the following publications: U.S. Pat. No. 5,534,390; DE 19503885A1, U.S. Pat. Nos. 5,484,696; 5,491,054, 5,200,307.

The compounds represented by the above formula A' serve as light stabilisers for the colour image and as agents against colour casts. They can be present in a photosensitive layer (colour layer) or in an interlayer, singly or together with other additives. Such compounds are described in more detail, inter alia, in the following publications: U.S. Pat. Nos. 3,700,455, 3,591,381, 3,573,052, 4,030,931, 4,174,220, 4,178,184, 4,228,235, 4,268,593, 4,279,990, 4,346,165, 4,366,226, 4,447,523, 4,528,264, 4,581,326, 4,562,146, 4,559,297, 5,534,390; GB-A-1,309,277,1,547,302, 2,023, 862, 2,135,788, 2,139,370, 2,156,091; DE-A-2,301,060, 2,347,708, 2,526,468, 2,621,203, 3,323,448, 19517072; DD-A-200,691, 214,468; EP-A-106,799,113,124,125,522, 159,912,161,577,164,030,167,762,176,845, 246, 766, 320, 776, 740204, 740205, 740206; JP-A-74/134,326, 76/127, 730, 76/30462, 77/3822, 77/154,632, 78/10842, 79/48535, 79/70830, 79/73032, 79/147,038, 79/154,325, 79/155,836, 82/142,638, 83/224,353, 84/5246, 84/72443, 84/87456, 84/192,246, 84/192,247, 84/204,039, 84/204,040, 84/212, 837, 84/220,733, 84/222,836, 84/228,249, 86/2540, 86/8843, 86/18835, 86/18836, 87/11456, 87/42245, 87/62157, 86/6652, 89/137,258 and in Research Disclosure 79/17804.

Hydroquinone compounds, which are useful as light stabilisers for the couplers and dyes and as oxidised developer scavengers, might also be contained in the photographic material according to this invention. Such compounds are predominantly used in magenta providing layers where the coupler is of the pyrazolone type and in interlayers. Such hydroquinone compounds and their combinations with other additives are described in more detail, inter alia, in the following publications:
U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572, 4,559,297, 5,491,054, 5,484,696; FR-A-885,982; GB-A-891,158, 1,156,167, 1,363,921, 2,022,274, 2,066,975, 2,071,348, 2,081,463, 2,117,526, 2,156,091; DE-A-2,408,168, 2,726,283, 2,639,930, 2,901,520, 3,308,766, 3,320,483, 3,323,699; DD-A-216,476, 214, 468, 214,469, EP-A-84290, 110,214, 115,305, 124, 915, 124,877, 144,288, 147, 747, 178,165, 161,577; JP-A-75/33733, 75/21249, 77/128,130, 77/146,234, 79/70036, 79/133,131, 81/83742, 81/87040, 81/109,345, 83/134,628, 82/22237, 82/112,749, 83/17431, 83/21249, 84/75249, 84/149,348, 84/182,785, 84/180,557, 84/189,342, 84/228,249, 84/101, 650, 79/24019, 79/25823, 86/48856, 86/48857, 86/27539, 86/6652, 86/72040, 87/11455, 87/62157, and in Research Disclosure 79/17901, 79/17905, 79/18813, 83/22827 and 84/24014.

Derivatives of hydroquinone ethers, which are particularly suitable for stabilising magenta dyes, might also be present. Such compounds and their combination with other additives are described in more detail e.g. in the following publications:
U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015, 4,559,297; GB-A 1,347,556, 1,366,441, 1,547,392, 1,557,237, 2,135, 788; DE-A 3,214,567; DD-214,469, EP-A 161,577, 167, 762, 164,130, 176,845; JP-A 76/123,642, 77/35633, 77/147,433, 78/126, 78/10430, 78/53321, 79/24019, 79/25823, 79/48537, 79/44521, 79/56833, 79/70036, 79/70830, 79/73032, 79/95233, 79/145,530, 80/21004, 80/50244, 80/52057, 80/70840, 80/139,383, 81/30125, 81/151,936, 82/34552, 82/68833, 82/204,306 82/204,037, 83/134,634, 83/207,039, 84/60434, 84/101,650, 84/87450, 84/149,348, 84/182,785, 86/72040, 87/11455, 87/62157, 87/63149, 86/2151, 86/6652, 86/48855, 89/309,058 and in Research Disclosure 78/17051.

The photographic layers can also contain certain phosphorus-III compounds, in particular phosphites and phosponites. These function as light stabilisers for the colour formers and as dark storage stabilisers for magenta couplers. They are preferably added to the high-boiling solvents, together with the coupler. Such phosphorus-III compounds are described in more detail e.g. in the following publications: U.S. Pat. Nos. 4,407,935, 4,436,811, 4,956,406, EP-A-181,289, JP-A-73/32728, JP-A-76/1420 and JP-A-55/66741.

The photographic layers can also contain organo-metallic complexes which are light stabilisers for the colour formers, in particular for the magenta dyes. Such compounds and their combination with other additives are described in more detail e.g. in the following publications: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, 4,590,153; JP-A-81/167,138, 81/168,652, 82/30834, 82/161,744; EP-A-137,271, 161,577, 185,506, 740,204; DE-A-2,853,865.

The photographic material according ot this invention might also contain conventional hindered amine light stabilisers, e.g. bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, bis(1-octyloxy-2,2,6,6-tetramethylpiperidin-4-yl)sebacate, n-butyl-3,5-di-tert-butyl-4-hydroxybenzyl-malonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the condensate of N,N'-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and also 4-butylamino-2,2,6,6-tetramethylpiperidine (CAS reg. No. [136504–96–6]); N-(2,2,6,6-tetramethyl-4-piperidyl)-n-dodecylsuccinimide, N-(1,2,2,6,6—pentamethyl-4-piperidyl)-n-dodecylsuccinimide, 2-undecyl-7,7,9,9-tetramethyl-1-oxa-3,8-diaza-4-oxo-spiro[4,5] decane, the reaction product of 7,7,9,9-tetramethyl-2-cycloundecyl-1-oxa-3,8-diaza-4-oxospiro [4,5]decane and epichlorohydrin, malonic acid[(4-methoxyphenyl)—methylenebis(1,2,2,6,6-pentamethyl-4-piperidyl)]-diester, N,N'-bis-formyl-N,N'-bis(2,2,6,6—tetramethyl-4-piperidyl)hexamethylenediamine, poly[methylpropyl-3-oxy-4-(2,2,6,6-tetramethyl-4-piperidyl)]siloxane, reaction product of maleic anhydride-α-olefin copolymer and 2,2,6,6-tetramethyl-4-aminopiperidine or 1,2,2,6,6-pentamethyl-4-aminopiperidine.

Further substances which might be used as light or dark stabilisers in the photographic material according to this invention are described in U.S. Pat. Nos. 5,580,710, 5,543,276, 3,700,455, 4,782,011, 5,316,903, 5,183,731, 5,070,007, 4,268,593 and DE 10006978.

Especially suited dye stabilisers are those of formulae (ST-1) to (ST-38). The stabilisers according to the present invention might be used in combination with them.

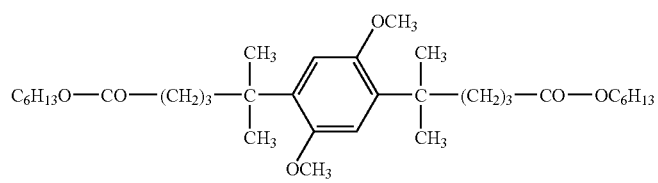

(ST-1)

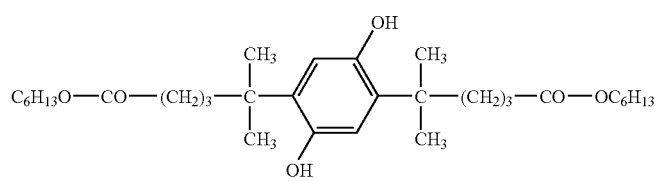

(ST-2)

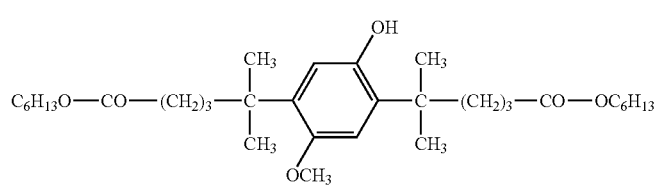

(ST-3)

-continued
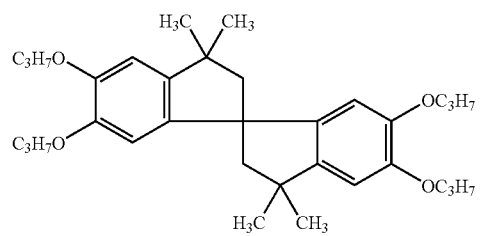 (ST-4)
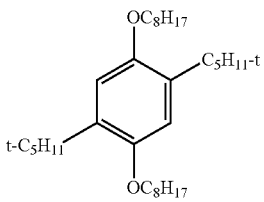 (ST-5)
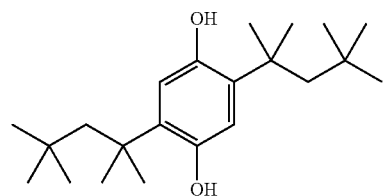 (ST-6)
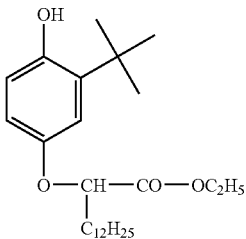 (ST-7)
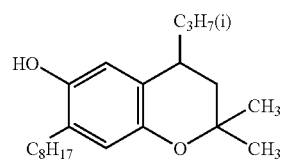 (ST-8)
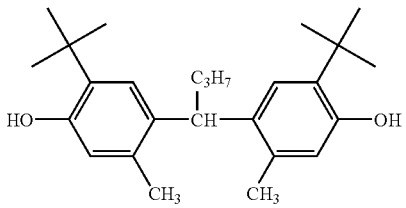 (ST-9)
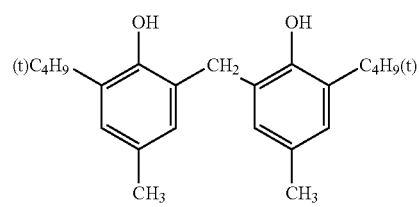 (ST-10)
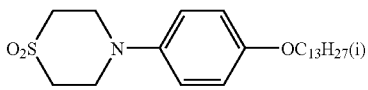 (ST-11)
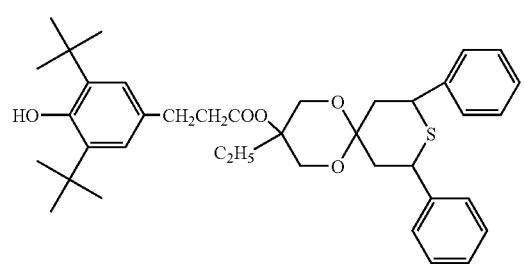 (ST-12)
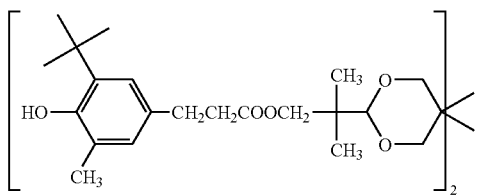 (ST-13)
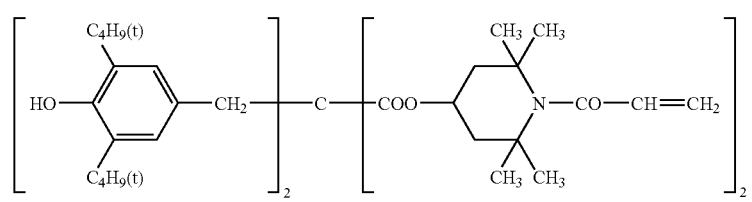 (ST-14)
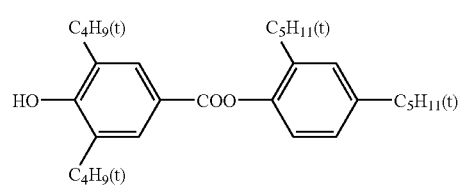 (ST-15)
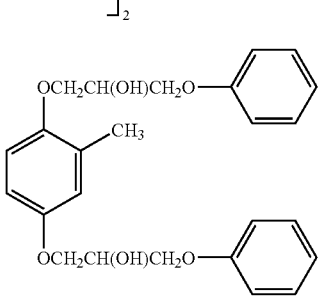 (ST-16)

(ST-17)
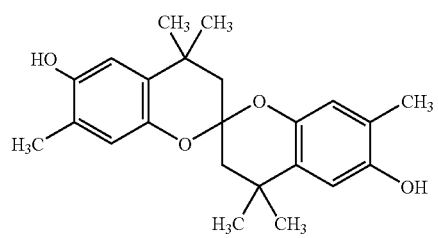
(ST-18)
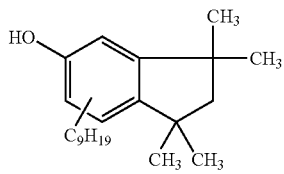
(ST-19)
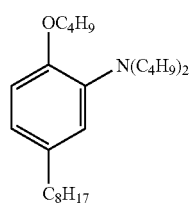
(ST-20)
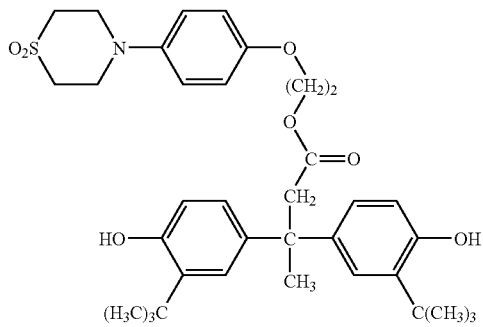
(ST-21)
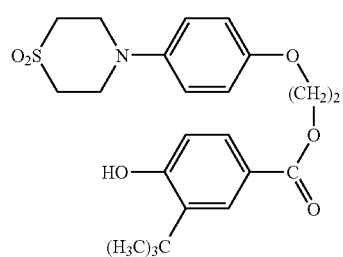
(ST-22)
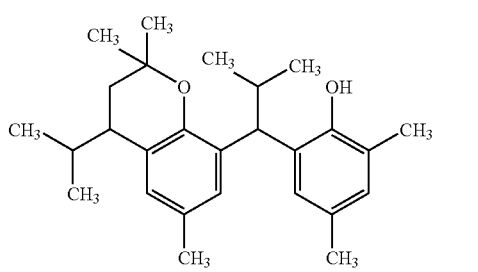
(ST-23)
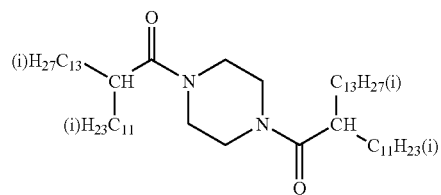
(ST-24)
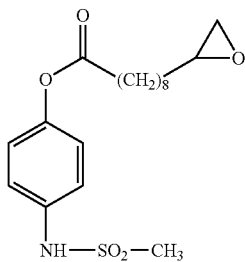
(ST-25)
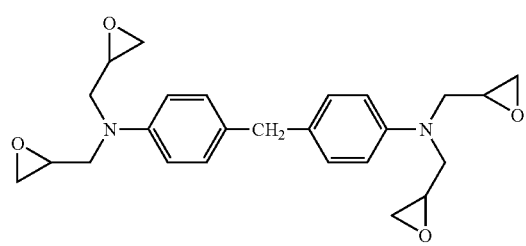
(ST-26)
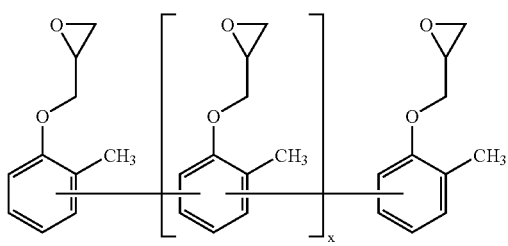
(ST-27)
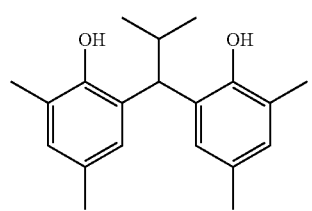
(ST-28)
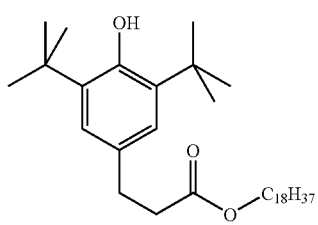

-continued
(ST-29)
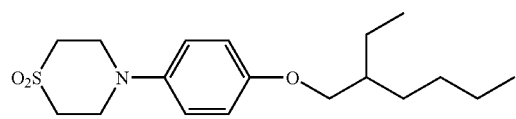
(ST-30)
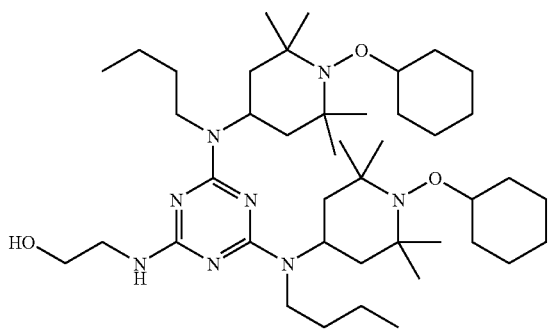
(ST-31)
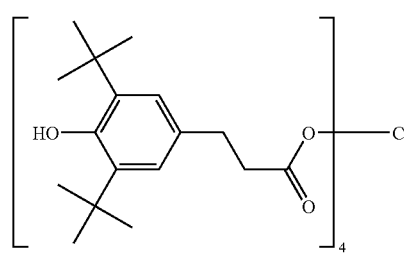
(ST-32)
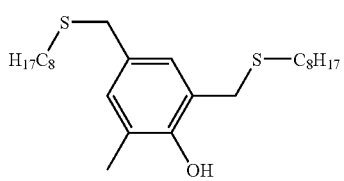
(ST-33)
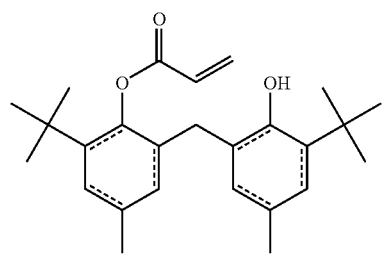
(ST-34)
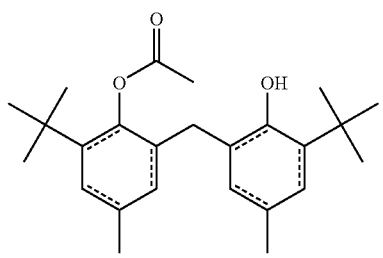
(ST-35)
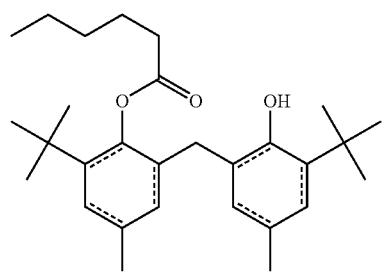
(ST-36)
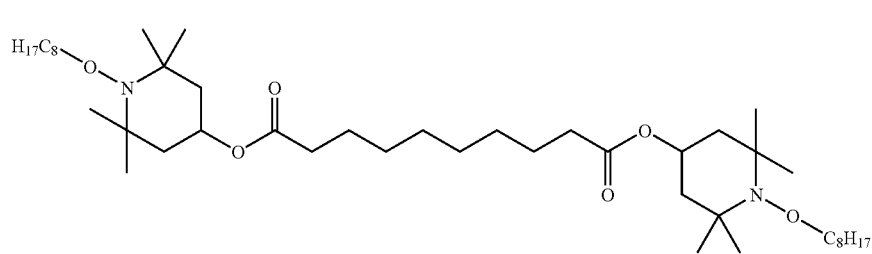
(ST-37)
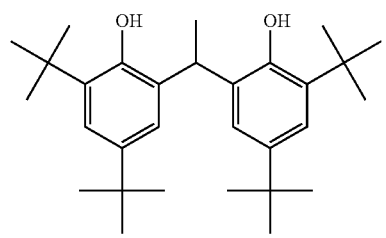

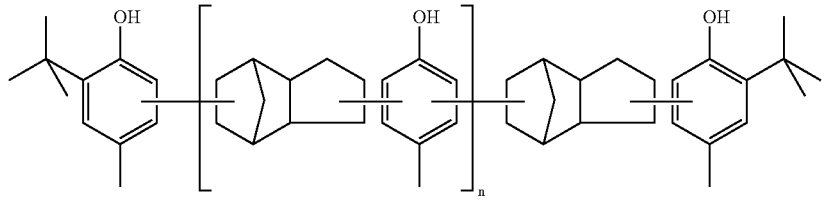
(ST-38)

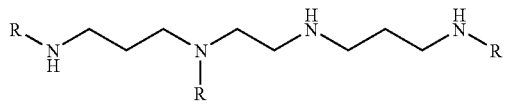
(ST-39)

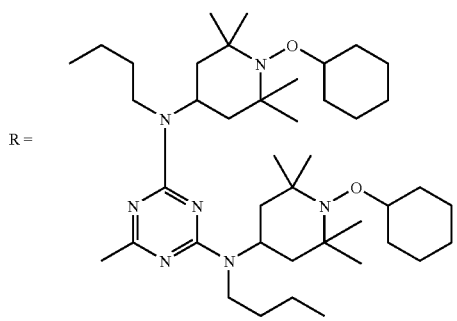

The layers of the photographic material can be cured using customary hardeners. Suitable hardeners are, for example, formaldehyde, glutaraldehyde and similar aldehyde compounds, diacetyl, cyclopentadione and similar ketone compounds, bis(2-chloroethylurea), 2-hydroxy-4,6-dichloro-1,3,5-triazine and other compounds containing reactive halogen (U.S. Pat. Nos. 3,288,775, 2,732,303, GB-A-974723 and GB-A-1167207), divinylsulfone compounds, 5-acetyl-1,3-diacryloylhexahydro-1,3,5-triazine and other compounds containing a reactive olefin bond (U.S. Pat. No. 3,635,718, U.S. Pat. No. 3,232,763 and GB-A-994869); N-hydroxymethylphthalimide and other N-methylol compounds (U.S. Pat. Nos. 2,732,316 and 2,586,168); isocyanates (U.S. Pat. No. 3,103,437); aziridine compounds (U.S. Pat. Nos. 3,017,280 and 2,983,611); acid derivatives (U.S. Pat. Nos. 2,725,294 and 2,725,295); carbodiimide type compounds (U.S. Pat. No. 3,100,704); carbamoylpyridinium salts (DE-A-2225230 and U.S. Pat. No. 2,439,511); carbamoylpyridinium compounds (DE-A-2408814); compounds containing a phosphorus-halogen bond (JP-A-113929/83); N-carbonyloximide compounds (JP-A-43353/81); N-sulfonyloximido compounds (U.S. Pat. No. 4,111,926), dihydroquinoline compounds (U.S. Pat. No. 4,013,468), 2-sulfonyloxypyridinium salts (JP-A-110762/81), formamidinium salts (EP-A-0162308), compounds containing two or more N-acyloximino groups (U.S. Pat. No. 4,052,373), epoxy., compounds (U.S. Pat. No. 3,091,537), isoxazole type compounds (U.S. Pat. Nos. 3,321,313 and 3,543,292); halocarboxyaldehydes, such as mucochloric acid; dioxane derivatives, such as dihydroxydioxan and dichlorodioxan; and inorganic hardeners, such as chrome alum and zirconium sulfate.

Curing can be effected in known manner by adding the hardener to the casting solution used for the layer to be cured, or by coating the layer to be cured with a layer containing a hardener capable of diffusion.

The classes listed here include both hardeners which act slowly and those which act rapidly, such as so-called instant hardeners which are particularly advantageous. Instant hardeners are understood to be compounds which crosslink suitable binders such that, immediately after casting, at the latest after 24 hours, preferably at the latest after 8 hours, curing is completed to such a degree that there is no change of the sensitometry and of the swelling of the layer compound caused by the crosslinking reaction. Swelling is understood to mean the difference between wet layer thickness and dry layer thickness when the film is processed in water (Photogr. Sci., Eng. 8 (1964), 275; Photogr. Sci., Eng. (1972), 449).

These hardeners which react very rapidly with gelatin are, for example, carbamoylpyridinium salts capable of reacting with free carboxyl groups of the gelatin so that the latter react with free amino groups of the gelatin with formation of peptide bonds and crosslinking of the gelatin.

There are hardeners capable of diffusion which act as hardeners for all layers within one multi-layer film. However, there are also low and high molecular weight hardeners, the action of which is restricted to one layer and which do not diffuse. Using these it is possible to crosslink individual layers, e.g. the protective layer, particularly strongly. This is important when the silver halide layer hardens little due to the silver hiding power and the mechanical properties must be improved with the protective layer (EP-A-0114699).

Colour photographic negative materials are usually processed by developing, bleaching, fixing and washing, or by developing, bleaching fixing and stabilising without subsequent washing, it being possible to combine bleaching and fixing to one processing step. The colour development compound used may be all developer compounds having the ability of reacting in the form of their oxidation product with colour couplers to azomethine or indophenol dyes. Suitable colour developer compounds are aromatic p-phenylenediamine type compounds containing at least one primary amino group, for example N,N-dialkyl-p-phenylenediamines such as N,N-diethyl-p-phenylenediamine, 1-(N-ethyl-N-methanesulfonamidoethyl)-3-methyl-p-phenylenediamine and 1-(N-ethyl-N-methoxyethyl)-3-methyl-p-phenylenediamine. Other suitable colour developers are described, for example, in J. Amer. Chem. Soc. 73, 3106 (1951) and G. Haist, Modern Photographic Processing, 1979, John Wiley and Sons, New York 545 ff.

Colour development may be followed by an acid stopping bath or washing.

The material is usually bleached and fixed immediately after colour development. Bleaches used may be, for example, Fe(III) salts and Fe(III) complex salts, such as ferricyanides, dichromates, water-soluble cobalt complexes. It is particularly preferred to use iron-(III) complexes of aminopolycarboxylic acids, in particular e.g. those of ethylenediaminetetraacetic acid, propylenediaminetetraacetic acid, diethylenetriaminepentaacetic acid, nitrilotriacetic acid, iminodiacetic acid, N-hydroxyethylethylenediamintriacetic-acid, alkyliminodicarboxylic acids and of corresponding phosphonic acids. Other suitable bleaches are persulfates and peroxides, e.g. hydrogen-peroxide.

The bleaching-fixing bath or fixing bath is usually followed by washing which is carried out as countercurrent washing or using several tanks with individual water inlets.

Favourable results can be obtained using a subsequent final bath which contains no, or only little, formaldehyde.

Washing can, however, be completely replaced by a stabilising bath which is usually carried out in countercurrent. If formaldehyde is added, this stabilising bath also functions as a final bath.

In the case of colour reversal materials, development is first carried out using a black-and-white developer, the oxidation product of which is not capable of reacting with the colour couplers. A subsequent diffuse secondary exposure is followed by development with a colour developer and then by bleaching and fixing.

Besides their use in colour photographic materials, compounds of formula (Ia), (Ib) or (IIc) can also find utility in other recording materials, such as digital recording materials, for example, those for pressure-sensitive copying systems, microcapsule photocopier systems, heat-sensitive copier systems and ink-jet printing.

The novel recording materials feature an unexpectedly high quality, especially in terms of their light stability.

The novel recording materials have a structure which is known per se and which corresponds to the utility. They consist of a base, for example paper or plastic film, on which one or more coatings are applied. Depending on the type of material, these coats contain the suitable components required, in the case of photographic material for example silver halide emulsions, colour couplers, dyes and the like. The material intended especially for ink-jet printing has a customary base on which there is an absorption layer suitable for ink. Uncoated paper can likewise be employed for ink-jet printing; in this case, the paper functions simultaneously as a base and has the absorbent for the ink. Suitable material for ink-jet printing is described, inter alia, in U.S. Pat. No. 5,073,448, the disclosure content of which is regarded as part of the present description.

The recording material can also be transparent, for example in the case of projection films.

The compound(s) of the invention can be incorporated into the material even in the course of manufacture; in papermaking, for example, by addition to the pulp. Another method of use is the spraying of the material with an aqueous solution of compound(s) of the invention, or the addition thereof to the coating.

Coatings for transparent recording materials for projection must not contain any light-scattering particles such as pigments or fillers.

The colour-binding coatings can contain further additives, for example antioxidants, light stabilisers (including UV absorbers), viscosity improvers, brighteners, biocides and/or antistats.

The coating is usually prepared as follows:

The water-soluble components, for example the binder, are dissolved in water and mixed.

The solid components, for example fillers and other additives as already described, are dispersed in this aqueous medium. Dispersion is advantageously brought about with the aid of equipment such as ultrasonic devices, turbine agitators, homogenisers, colloid mills, bead mills, sand mills, high-speed stirrers and the like. A particular advantage of the compounds of the invention is their ease of incorporation into the coating.

As mentioned, the novel recording materials cover a broad field of use. Compounds of the invention can be employed, for example, in pressure-sensitive copier systems. They can be added to the paper to protect the microencapsulated dye precursors against light, or to the binder of the developer layer to protect the dyes formed therein.

Photocopier systems with light-sensitive microcapsules which are developed by pressure are described, inter alia, in U.S. Pat. Nos. 4,416,966; 4,483,912; 4,352,200; 4,535,050; 4,5365,463; 4,551,407; 4,562,137 and 4,608,330; and also in EP-A-139,479; EP-A-162,664; EP-A-164,931; EP-A-237,024; EP-A-237,025 and EP-A-260,129. In all these systems the compounds of the invention can be added to the colour-accepting layer. Alternatively, the compounds of the invention can be added to the donor layer for protecting the colour formers against light.

The compounds of the invention can also be employed in recording materials which are based on the principle of photopolymerisation, photosoftening or the rupture of microcapsules, or when heat-sensitive or photosensitive diazonium salts, leuco dyes with oxidising agent or colour lactones with Lewis acids are used.

Heat-sensitive recording material exploits the colour-imparting reaction between a colourless or weakly coloured base dye and an organic or inorganic colour developer, the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the invention. If the said protective layer is present, the compounds of the invention can also be incorporated into the protective layer.

Heat-sensitive recording materials are described, for example, in JP-A 8–267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing, as are described, for example, in EP-A-507,734.

The novel recording material preferably contains 1 to 10,000 mg/m$^2$, in particular 50–2,000 mg/m$^2$, of at least one compound of the formulae (Ia), (Ib) or (IIc).

Compounds of the invention can also be employed in inks, preferably for ink-jet printing, for example those as described in U.S. Pat. No. 5,098,477, the disclosure content of which is regarded as part of the present description. The invention therefore also provides an ink comprising at least one compound of the invention as stabiliser. The inks according to the invention contain at least one dye. In this regard the nature of the ink and the dye dissolved in it and the type of printer used are immaterial. The ink, especially for ink-jet printing, contains preferably water.

In many printers a distinction is drawn between those which have a continuous ink jet and "drop-on-demand" printers, in particular bubble-jet printers. The ink according to the invention can be used for the equipment of all these processes, specifically for printing ink jet printing paper and films.

The inks are in most cases aqueous inks, but they can also be solutions of the dye in an organic solvent or in a melted wax. In most cases aqueous inks still contain water-soluble solvents, for example mono-, di- or tri-ethylene glycols or higher ethylene glycols, propylene glycol, 1,4-butanediol or ethers of such glycols, thiodiglycol, glycerol and ethers and esters thereof, polyglycerol, mono-, di- and tri-ethanolamine, propanolamine, dimethylformamide, dimethyl sulfoxide, dimethylacetamide, N-methylpyrrolidone, 1,3-dimethylimidazolidone, methanol, ethanol, isopropanol, n-propanol, diacetone alcohol, acetone, methyl ethyl ketone or propylene carbonate.

Aqueous inks contain water-soluble dyes such as are also known for dyeing natural fibers. These can, for example, be monoazo, disazo or polyazo dyes, reactive dyes, triphenylmethane dyes, xanthene dyes or phthalocyanine dyes. Examples of these are Food Black 2, C.I. Direct Black 19, C.I. Sulphur Black 1, Acid Red 35, Acid Red 52, Acid Yellow 23 and copper phthalocyanines, and also Direct Black 38, Direct Black 168, Acid Red 249, Direct Red 227, Direct Yellow 86, Acid Blue 9, Direct Blue 86 and Direct Blue 199. Aqueous inks can also contain various additives in minor amounts, for example binders, surfactants, biocides, corrosion inhibitors, sequestering agents, pH buffers or conductivity additives. They can also contain water-soluble UV absorbers or other water-soluble light stabilizers. In general, however, the addition, according to the invention, of a stabilizer of the formula I to the ink is adequate.

If the ink is a non aqueous ink, it is a solution of the dye in an organic solvent or solvent mixture. Examples of solvents used for this purpose are alkyl carbitols, alkylcellosolves, dialkylformamides, dialkylacetamides, alcohols, especially alcohols having 1–4 C atoms, acetone, methyl ethyl ketone, diethyl ketone, methyl isobutyl ketone, diisopropyl ketone, dibutyl ketone, dioxane, ethyl butyrate, ethyl isovalerate, diethyl malonate, diethyl succinate, methyl pelargonate, butyl acetate, triethyl phosphate, ethylglycol acetate, toluene, xylene, tetralin or petroleum fractions. Examples of solid waxes as solvents, which, as an ink, must first be heated, are stearic or palmitic acid.

Inks of this type based on solvents contain dyes soluble therein, for example Solvent Red, Solvent Yellow, Solvent Orange, Solvent Blue, Solvent Green, Solvent Violet, Solvent Brown or Solvent Black. Inks of this type too can also contain further additives, such as are mentioned above for aqueous inks.

Inks contain the stabiliser of the invention usually in a concentration of from 0.01 to 20% by weight, in particular from 0.5 to 10% by weight.

EXAMPLES

Example 1 (Preparation according WO99/46261)

Preparation of 2,2,6,6-tetramethyl-1-(1-(4-oxiranyl-methoxy-phenyl)-ethoxy)-4-propoxypiperidine Compound II with A=—CH$_2$—CHY—CH$_2$—; Y=OR$_{14}$, R$_3$=—C(R$_{10}$)$_2$—X—D, R$_{10}$=H, CH$_3$, X=phenylene, D=

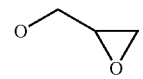

A: A 70% aqueous solution of tert.-butylhydroperoxyde (26.4 g) is extractively dehydrated in two portions with each of 25 g 2-(4-ethyl-phenoxymethyl)-oxirane. The organic extracts are combined, a molecular sieve is added and the mixture is stored under argon atmosphere.

B: A mixture of 2-(ethyl-phenoxymethyl)-oxirane (57 g), 4-propoxy-2,2,6,6-tetramethylpiperidine-1-oxyl (10.7 g) and molybdenum(VI)oxide (0.72 g) are purged with Argon for one hour. The mixture is then heated up to 70° C. and the solution prepared under A) is added under stirring within 30 minutes. Pressure is reduced to 200 mbar and the mixture is heated for 18 hours at 100° C. After the reaction is completed the mixture is cooled to room temp. and the pressure is allowed to raise to normal pressure. Ethylacetate and water is added. The water phase is separated and extracted once with ethylacetate. The organic phases are combined, washed with a 10% solution of sodium ascorbate and in a second step with water, dried over sodium sulfate and concentrated. Excessive amounts of 2-(4-ethyl-phenoxymethyl)-oxirane are removed at 80° C./0.01 mbar. The raw product is subsequently chromatographically purified on silica with petrolether/ethylacetate 7/1 as eluent. A clear colorless oil is obtained, corresponding to the compound of formula (101)

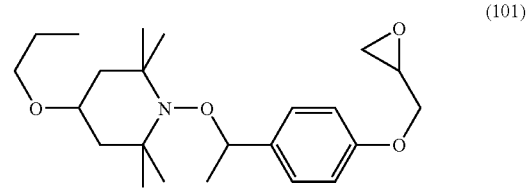

(101)

Elemental Analysis: calculated C$_{23}$H$_{37}$NO$_4$: 70.55%, C; 9.52%, H; 3.57%, N. found: 70.66%, C; 9.60%, H; 3.43%, N.

Example 2 (Preparation According to WO02/48109)

Preparation of 7,7,9,9-tetramethyl-8-[1-(4-oxiranyl-methoxy-Phenyl)-ethoxy]-1.4-dioxa-8-aza-spiro[4.5]decan Compound II with A=—CH$_2$—C(OZ)(OZ')—CH$_2$—; Z and Z' form a bivalent group —CH$_2$—CH$_2$—, R$_3$=—C(R$_{10}$)$_2$—X—D, R$_{10}$=H, CH$_3$, X=phenylene, D=

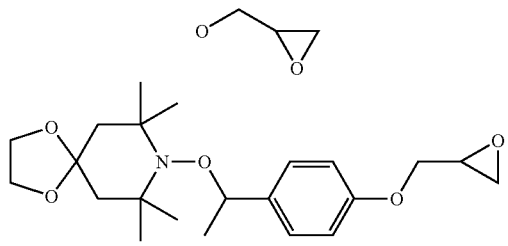

A mixture of 50 g 7,7,9,9-tetramethyl-1,4-dioxa-8-aza-spiro[4.5]decan-8-oxyl (prepared according to EP 574666A1) and 124.75 g 2-(4-ethyl-phenoxymethyl)-oxiran are heated to 600° C. with stirring and a solution of 0.32 g copper(II)chloride in 1.6 ml ethanol is added. 45 g of an aqueous solution of butylhydroperoxide in water (70%) is dropwise added. The reaction mixture is allowed to further react for 16 h at 60° C. and subsequently cooled to room temperature. Excess tert.-butylhydroperoxide is removed by dropwise adding 15 ml of an aqueous sodium pyrosulfite solution. To the reaction mixture 100 ml acetic acid ethylester are added and the organic and aqueous phase are separated. The organic phase is washed twice with 200 ml of a saturated NaCl solution. After drying with sodium sulfate and evaporation of the solvent an oil is obtained, from which excess 2-(4-ethyl-phenoxymethyl)-oxiran is removed by distillation (100° C./0.005 mbar). The residue is dissolved in hexane filtered over aluminium oxide and the solvent is again evaporated. After recrystallization from hexane white crystals are obtained having a melting point of 73.5–74.2° C.

Example 3

Preparation of 3,3,8,8,10,10-hexamethyl-9-[1-(4-oxiranylmethoxy-phenyl)-ethoxy]-1,5-dioxa-9-aza-spiro[5.5]undecan Compound II with A=—CH$_2$—C(OZ)(OZ')—CH$_2$—; Z and z form a bivalent group —CH$_2$—C(CH$_3$)(CH$_3$)CH$_2$—, R$_3$=—C(R$_{10}$)$_2$—X-D, R$_{10}$=H, CH$_3$, X=phenylene, D=

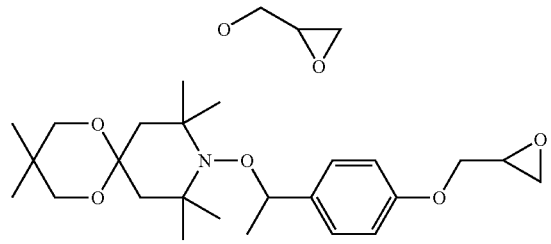

The title compound is prepared in analogy to Example 2 from 3,3,8,8,10,10-hexamethyl-1,5-dioxa-9-aza-spiro[5.5]undecan-9-oxyl (prepared according to EP 574666A1). White crystals are obtained.

Elemental analysis: calculated: 69.25%, C; 9.07%, H; 3.23%, N; found: 68.86%, C; 9.05%, H; 3.18%, N.

Preparation of the New Compounds

Example 4

Preparation of 1-Dimethylamino-3-[4-[1-(3,3,8,8,10,10-hexamethyl-1,5-dioxa-9-aza-spiro[5.5]undec-9-yloxy)-ethyl]-phenoxy]-propan-2-ol Compound II with A=—CH$_2$—C(OZ)(OZ)—CH$_2$—; Z and Z' form a bivalent group —CH$_2$—C(CH$_3$)(CH$_3$)CH$_2$—, R$_3$=—C(R$_{10}$)$_2$—X—D, R$_{10}$=H, CH$_3$, X=phenylene, D=—O—CH$_2$—CH(OH)—CH$_2$—N(CH$_3$)$_2$

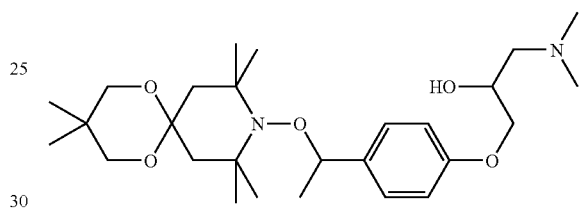

A solution of 4.33 g 3,3,8,8,10,10-Hexamethyl-9-[1-(4-oxiranylmethoxy-phenyl)-ethoxy]-1,5-dioxa-9-aza-spiro[5.5]undecane prepared according to PCT/EP/01/13071 and 1.46 g diethylamine in methanol (15 ml) was stirred at reflux for 2 h. After evaporation of methanol a highly viscous resin was obtained. Stirring the resin in water (100 ml) for two days gave a white suspension. The suspension was filtered and washed with water. After vacuum drying a colourless powder was obtained having a melting point of 77–83° C.

Example 5

Preparation of 1-[4-[1-(3,3,8,8,10,10-Hexamethyl-1,5-dioxa-9-aza-spiro[5.5]undec-9-yloxy)-ethyl]-phenoxy}-3-pyrrolidin-1-yl-propan-2-ol Compound II with A=—CH$_2$—C(OZ)(OZ')—CH$_2$—; Z and Z' form a bivalent group —CH$_2$—C(CH$_3$)(CH$_3$)CH$_2$—, R$_3$=—C(R$_{10}$)$_2$—X—D, R$_{10}$=H, CH$_3$, X=phenylene, D=—O—CH$_2$—CH(OH)—CH$_2$—N(R$_{12}$)(R$_{13}$); R$_{12}$ and R$_{13}$ form a ring

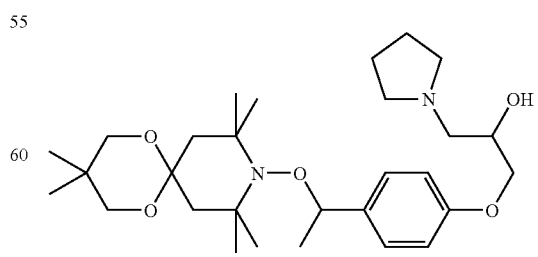

The compound of Example 5 is prepared according to Example 4 using pyrrolidine.

Example 6

Preparation of 1-Diethylamino-3-[4-[1-(3,3,8,8,10,10-hexamethyl-1,5-dioxa-9-aza-spiro[5.5]undec-9-yloxy)-ethyl]-phenox}-propan-2-ol Compound II with A=—CH$_2$—C(OZ)(OZ')—CH$_2$—; Z and Z' form a bivalent group —CH$_2$—C(CH$_3$)(CH$_3$)CH$_2$—, R$_3$=—C(R$_{10}$)$_2$—X—D, R$_{10}$=H, CH$_3$, X=phenylene, D=—O—CH$_2$—CH(OH)—CH$_2$—N(C$_2$H$_5$)$_2$

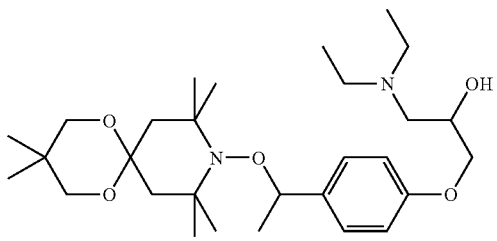

The compound of Example 6 is prepared according to Example 4 using diethylamine.

Example 7

Preparation of 1-{4-[1-(3,3,8,8,10,10-Hexamethyl-1,5-dioxa-9-aza-spiro[5.5]undec-9-yloxy)-ethyl]-phenoxy}-3-[4-(3-{4-[1-(3,3,8,8,10,10-hexamethyl-1,5-dioxa-9-aza-spiro[5.5]undec-9-yloxy)-ethyl]-phenoxy}-2-hydroxy-propyl)-piperazin-1-yl]-propan-2-ol Compound II with A=—CH$_2$—C(OZ)(OZ')—CH$_2$—; Z and Z' form a bivalent group —CH$_2$—C(CH$_3$)(CH$_3$)CH$_2$—, R$_3$=—C(R$_{10}$)$_2$—X—D', R$_{10}$=H, CH$_3$, X=phenylene D'=—O—CH$_2$—CH(OH)—CH$_2$-piperazine-CH$_2$—CH(OH)—CH$_2$—O—,

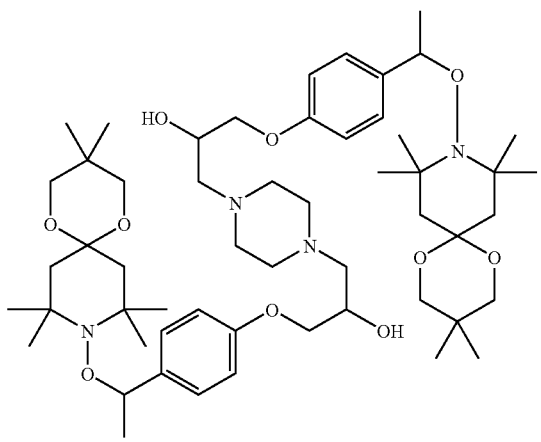

To a solution of 8,67 g 3,3,8,8,10,10-Hexamethyl-9-[1-(4-oxiranylmethoxy-phenyl)-ethoxy]-1,5-dioxa-9-aza-spiro[5.5]undecane in tetrahydrofurane (24 ml) was added 0,86 g piperazine. The reaction mixture was stirred at reflux over night then evaporated to dryness. The resinous residue is stirred in methanol (25 ml) until a homogenous suspension was formed. The suspension was filtered, the residue washed with icecold methanol (15 ml) and dried at room temperature. A white powder was obtained melting at 137–142° C.

Example 8

Butyl-(2-hydroxy-3-{4-[1-(2,2,6,6-tetramethyl-4-propoxy-piperidin-1-yloxy)-ethyl]-phenoxy}-propyl)-amino]-3-{4-[1-(2,2,6,6-tetramethyl-4-propoxy-piperidin-1-yloxy)-ethyl]-phenoxy}-propan-2-ol Compound II with A=—CH$_2$—CH(Y)—CH$_2$—; Y is alkoxy;
R$_3$=—C(R$_{10}$)$_2$—X-D', R$_{10}$=H, CH$_3$, X=phenylene, D'=—O—CH$_2$—CH(OH)—CH$_2$—N(alkyl)-CH$_2$—CH(OH)—CH$_2$—O—,

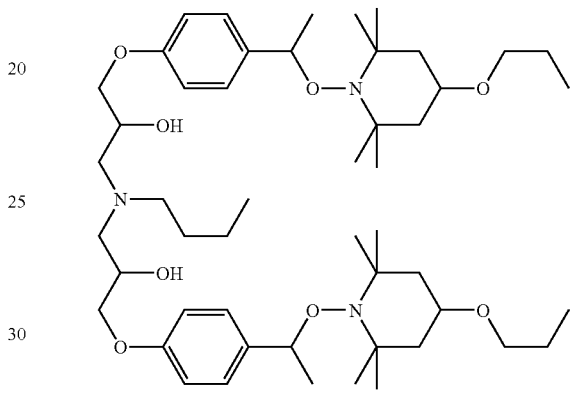

Example 8 is prepared according to Example 7 using butylamine.

Example 9

Compound II with A=—CH$_2$—CH(Y)—CH$_2$—; Y is alkoxy,
R$_3$=—C(R$_{10}$)$_2$—X—D', R$_{10}$=H, CH$_3$, X=phenylene,
D'=—(O—CH$_2$—CH(OH)—CH$_2$—)$_2$—N—CH$_2$—CH$_2$—N—(CH$_2$—CH(OH)—CH$_2$—O)$_2$—,

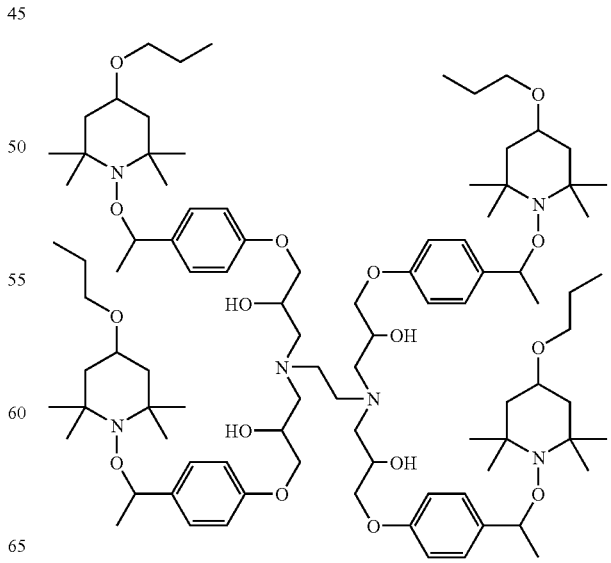

Example 9 is prepared according to Example 7 using ethylendiamine.

APPLICATION EXAMPLES

Example A1

Photographic test elements are prepared by providing layers of following composition on a polyethylene-coated paper support:

| Component | Amount in mg · m$^{-2}$ |
|---|---|
| Gelatine | 5150 |
| AgBr | 520 (based on silver) |
| Yellow coupler Y1 | 973 |
| Stabilizer according to invention | 292 |
| Dibutylphthalate | 324 |
| Hardener H1 | 300 |
| Surfactant S1 | 340 |
| Antifoggant A1 | 4 |

After drying, the produced samples are exposed to white light behind a step wedge with density increment 0.30 and thereafter processed in the customary manner according to the P94 process (Agfa-Gevaert).

The samples are then evaluated for light fastness by exposing them through an ultraviolet filter in an Atlas weatherometer equipped with a Xenon lamp. The light fastness is evaluated based on the percentage of density loss after 60 kJ.cm$^{-2}$ exposure.

In a second experiment, yellow step images obtained in the above described way are stored in the dark at 80° C., 70% relative humidity. The dark stability is evaluated based on the percentage of density loss after 4 weeks storage.

TABLE I

| Sample | Stabilizer | Density loss (%) upon Xenon exposure at density | | Density loss (%) upon dark storage at density | |
|---|---|---|---|---|---|
| | | 1.0 | D$_{max}$ | 1.0 | D$_{max}$ |
| I-1 (control) | — | 60 | 78 | 36 | 37 |
| I-2 (comparison) | ST-12 | 29 | 38 | 32 | 34 |
| I-3 (comparison) | ST-33 | 32 | 25 | 36 | 28 |
| I-4 (comparison) | ST-39 | 39 | 59 | 36 | 36 |
| I-5 (invention) | ST-A | 19 | 7 | 31 | 32 |
| I-6 (invention) | ST-B | 16 | 3 | 20 | 30 |
| I-7 (invention) | ST-C | 17 | 8 | 27 | 29 |
| I-8 (invention) | ST-D | 21 | 11 | 29 | 32 |
| I-9 (invention) | ST-E | 16 | 7 | 28 | 28 |

As table I shows, the compounds according to the invention provide the yellow image with much improved light stability, especially at high density. In addition, improved dark stability of the yellow dye is achieved.

Example A2

Photographic test elements are prepared by providing layers of following composition on a polyethylene-coated paper support:

| Component | Amount in mg · m$^{-2}$ |
|---|---|
| Gelatine | 5150 |
| AgBr | 520 (based on silver) |
| Yellow coupler Y2 | 859 |
| Stabilizer according to invention | 258 |
| Dibutylphthalate | 286 |
| Hardener H1 | 300 |
| Surfactant S1 | 340 |
| Antifoggant A1 | 4 |

After drying, the produced samples are exposed to white light behind a step wedge with density increment 0.30 and thereafter processed in the customary manner according to the P94 process (Agfa-Gevaert).

The samples are then evaluated for light fastness by exposing them through an ultraviolet filter in an Atlas weatherometer equipped with a Xenon lamp. The light fastness is evaluated based on the percentage of density loss after 90 kJ.cm$^{2}$ exposure.

TABLE II

| Sample | Stabilizer | Density loss (%) upon Xenon exposure at density | |
|---|---|---|---|
| | | 1.0 | D$_{max}$ |
| II-1 (control) | — | 27 | 42 |
| II-2 (comparison) | ST-33 | 21 | 12 |
| II-3 (comparison) | ST-39 | 22 | 20 |
| II-4 (comparison) | ST-26 | 23 | 29 |
| II-5 (invention) | ST-A | 21 | 9 |
| II-6 (invention) | ST-B | 15 | 4 |
| II-7 (invention) | ST-C | 22 | 12 |
| II-8 (invention) | ST-D | 20 | 9 |
| II-9 (invention) | ST-E | 21 | 6 |

The above table shows that the compounds according to the invention improve substantially the light stability of the yellow photographic image, especially at high density.

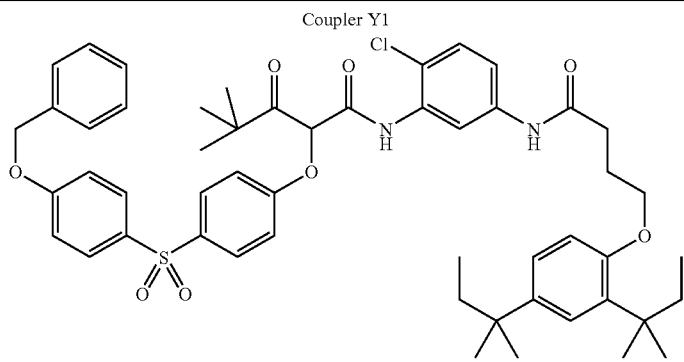
Coupler Y1
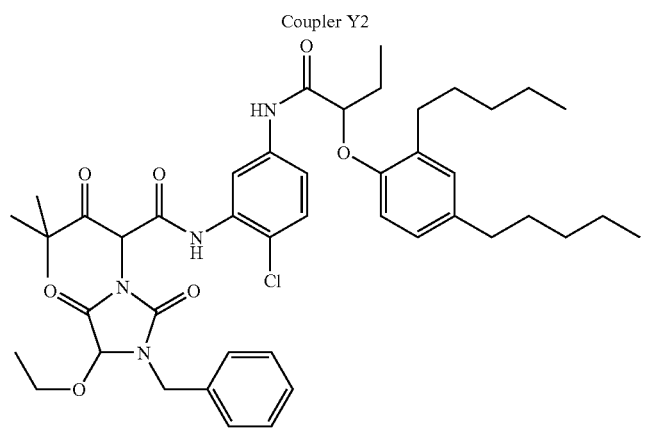
Coupler Y2
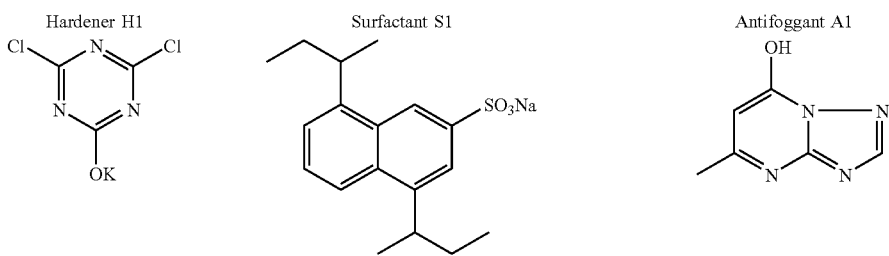
Hardener H1  Surfactant S1  Antifoggant A1
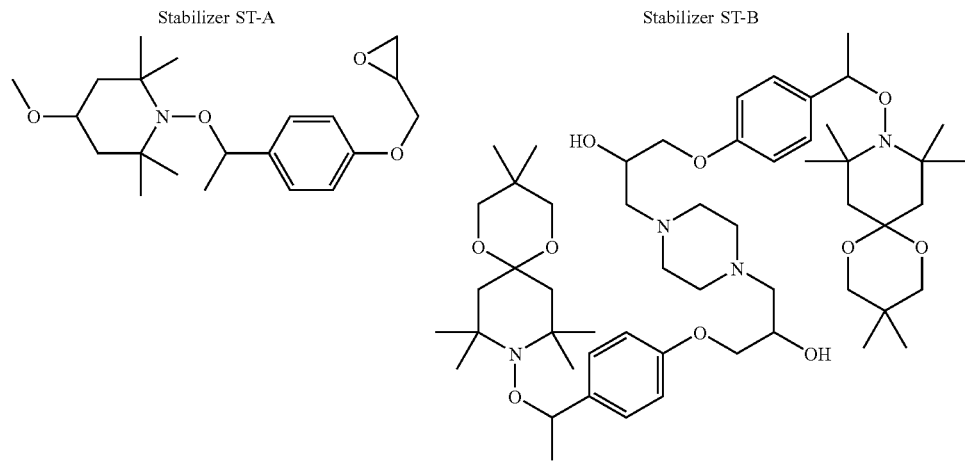
Stabilizer ST-A  Stabilizer ST-B

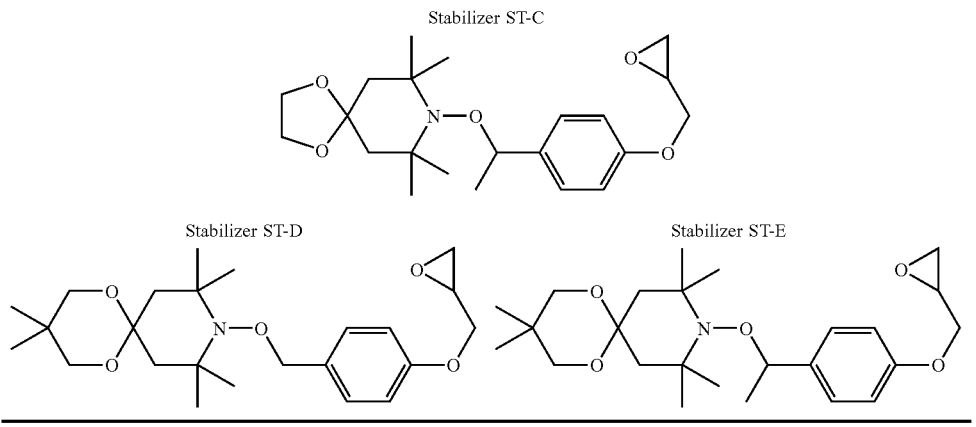

The invention claimed is:

1. A colour photographic material which contains on a support at least one blue-sensitive silver halide emulsion layer containing at least one yellow coupler, at least one green-sensitive silver halide emulsion layer containing at least one magenta coupler, at least one red-sensitive silver halide emulsion layer containing at least one cyan coupler, together with non-light-sensitive layers, wherein at least one layer contains a compound of the formula (I) or (II)

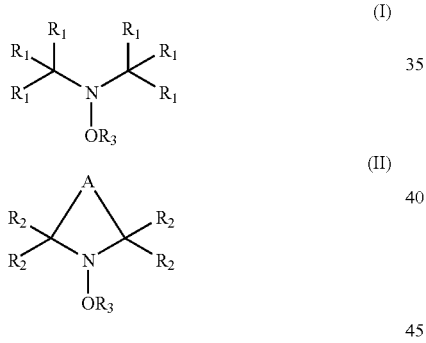

wherein
the $R_1$-radicals are each independently of one another hydrogen, halogen, $NO_2$, cyano, —$CONR_5R_6$, —($R_9$)$COOR_4$, —C(O)—$R_7$, —$OR_8$, —$SR_8$, —$NHR_8$, —$N(R_8)_2$, carbamoyl, di($C_1$–$C_{18}$alkyl)carbamoyl, —C(=$NR_5$)($NHR_6$);
unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_2$–$C_{12}$heterocycloalkyl; or $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_2$–$C_{12}$heterocycloalkyl, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)-amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino;
$R_4$ is hydrogen, $C_1$–$C_{18}$alkyl, phenyl, an alkali metal cation or a tetraalkylammonium cation;
$R_5$ and $R_6$ are hydrogen, $C_1$–$C_{18}$alkyl, $C_2$–$C_{18}$alkyl, which is substituted by at least one hydroxy group or, taken together, form a $C_2$–$C_{12}$alkylene bridge or a $C_2$–$C_{12}$-alkylene bridge interrupted by at least one O or $NR_8$ atom;
$R_7$ is hydrogen, $C_1$–$C_{18}$alkyl or phenyl;
$R_8$ is hydrogen, $C_1$–$C_{18}$alkyl or $C_2$–$C_{18}$alkyl which is substituted by at least one hydroxy group;
$R_9$ is $C_1$–$C_{12}$alkylene or a direct bond; or
all the $R_1$-radicals form together the residue of a polycyclic cycloaliphatic ring system or a polycyclic heterocycloaliphatic ring system with at least one di- or trivalent nitrogen atom;
the $R_2$-radicals are independently of each other $C_1$–$C_6$alkyl or phenyl;
$R_3$ is a radical of the formula —C($R_{10})R_{10}$)—X—D, wherein
X is phenylene, naphthylene or biphenylene, which are unsubstituted or substituted by NO2, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;
the $R_{10}$-radicals are independently of each other H or $CH_3$;
D is a group

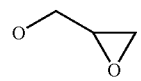

or a group —C(O)—$C_1$–$C_{18}$alkyl or
a group —C(O)—$R_{11}$—C(O)—$C_1$–$C_{18}$alkyl; with $R_{11}$ being a bond or $C_1$–$C_{12}$alkylene, or
a group —O—$CH_2$—CH(OH)—$CH_2$—$NR_{12}R_{13}$, wherein
$R_{12}$ and $R_{13}$ independently of one another are unsubstituted $C_1$–$C_{18}$alkyl, $C_2$–$C_{18}$alkenyl, $C_2$–$C_{18}$alkynyl, phenyl, $C_7$–$C_9$phenylalkyl, $C_3$–$C_{12}$cycloalkyl; the radicals may be interrupted once or more than once by —, —NH—, —O—, —S—, —CO—, —SO—, —$SO_2$—, or
$C_1$–$C_{18}$alkyl, $C_2$–$C_{18}$alkenyl, $C_2$–$C_{18}$ alkynyl, phenyl, $C_7$–$C_9$phenylalkyl, $C_3$–$C_{12}$cycloalkyl, which are substituted by halogen, amino, hydroxy, carboxy, $C_1$–$C_6$alkoxy, $C_1$–$C_6$alkoxycarbonyl, $C_1$–$C_6$alkylthio, $C_1$–$C_6$alkylamino or di($C_1$–$C_6$alkyl)-amino, $C_1$–$C_6$alkylamino-carbonyl or di($C_1$–$C_6$alkyl)-amino-carbonyl; the radicals may be interrupted once or more than once by —, —NH—, —O—, —S—, —CO—, —SO—, —SO$_2$—, or $R_{12}$ and $R_{13}$ together with N form a 4 to 8 membered ring, whereby the ring may be interrupted by —O—, —NH—, S—, —CO—, —SO—, —SO$_2$ and may be sustituted by carboxy, or D is a group —O—CH$_2$—CH(OH)—CH$_2$—N($R_{12}$)—CH$_2$—CHOH—CH$_2$—O— or —O—CH$_2$—CH(OH)—CH$_2$—W—CH$_2$—CHOH—CH$_2$—O— with W being a divalent amino group (—N($R_{12}$)—), a polyamine residue, a polyethyleneimine residue or a polyoxyalkyleneamine residue;

A is a divalent group required to form a cyclic 5-, 6- or 7-membered ring, whereby the divalent group is selected from $C_2$–$C_4$alkylene, $C_2$–$C_4$alkenylene, $C_2$–$C_4$alkinylene, 1,2 phenylene which may be unsubstituted or substituted by NO$_2$, halogen, amino, hydroxy, cyano, carboxy, carbonyl, $C_1$–$C_{18}$alkoxy, $C_1$–$C_{18}$ acyloxy, benzoyloxy, $C_1$–$C_{18}$alkylthio, $C_1$–$C_{18}$alkylamino or di($C_1$–$C_{18}$alkyl)amino, or phenyl; or A is a group —CH$_2$—CHY—CH$_2$—, wherein Y is H, OH, OR$_{14}$, NR$_{15}$R$_{16}$, —O—C(O)—R$_{17}$ or NR$_{15}$—C(O)—R$_{17}$;

$R_{14}$ is $C_1$–$C_{18}$alkyl, $C_2$–$C_{18}$alkenyl, $C_2$–$C_{18}$alkinyl, phenyl, benzyl, mesityl, or $C_2$–$C_{18}$alkyl which is substituted by at least one hydroxy group;

$R_{15}$ and $R_{16}$ independently are hydrogen, $C_1$–$C_{18}$alkyl, $C_2$–$C_{18}$alkenyl, $C_2$–$C_{18}$alkinyl, or taken together form a $C_2$–$C_{12}$alkylene bridge or a $C_2$–$C_{12}$alkylene bridge interrupted by at least one O atom;

$R_{17}$ is phenyl, benzyl, mesityl, $C_1$–$C_{18}$alkyl, $C_2$–$C_{18}$alkenyl, $C_2$–$C_{18}$alkinyl; or A is a group —CH$_2$—C(OZ)(OZ')—CH$_2$—, wherein Z and Z' are independently $C_1$–$C_{12}$alkyl, $C_3$–$C_{12}$alkenyl, $C_3$–$C_{12}$alkinyl, $C_5$–$C_8$cycloalkyl, phenyl, naphthyl, $C_7$–$C_9$phenylalkyl; or Z and Z' together form one of the bivalent groups —C($R_{18}$)($R_{19}$)—CH($R_{20}$)—, —CH($R_{18}$)—CH$_2$—C($R_{19}$)($R_{20}$)—, —CH($R_{19}$)—CH$_2$—C($R_{18}$)($R_{20}$)—, —CH$_2$—C($R_{18}$)($R_{19}$)—CH($R_{20}$)-o-phenylene, 1,2-cyclohexylidene, —CH$_2$—CH═CH—CH$_2$— or

wherein $R_{18}$ is hydrogen, $C_1$–$C_{18}$alkyl, COOH, COO—($C_1$–$C_{18}$)alkyl, OCO—($C_1$–$C_{18}$)alkyl or CH$_2$OR$_{21}$;

$R_{19}$ and $R_{20}$ are independently hydrogen, $C_1$–$C_{12}$alkyl, COOH or COO—($C_1$–$C_{12}$)alkyl;

$R_{21}$ is hydrogen, $C_1$–$C_{18}$alkyl, $C_5$–$C_6$cycloalkyl, benzyl, or a monovalent acyl residue derived from an aliphatic, cycloaliphatic or aromatic monocarboxylic acid having up to 18 carbon atoms; or Z and Z' together form one of the tetravalent groups

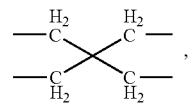

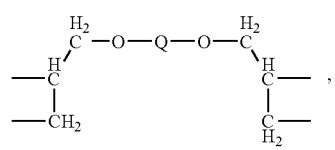

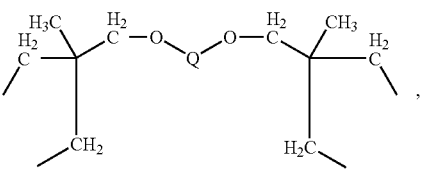

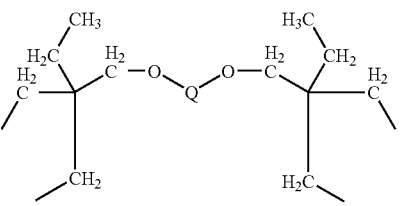

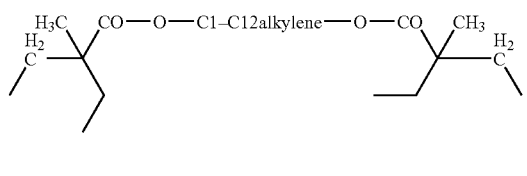

wherein

Q is a bisacyl residue which is derived from a $C_2$–$C_{12}$dicarboxylic acid or $C_1$–$C_{12}$alkylene.

2. A colour photographic material according to claim 1, containing a compound of the formula I, wherein $R_1$ is methyl and $R_3$ is a radical —CH(CH$_3$)—X—D, wherein X is phenylene, D is a group

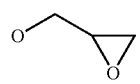

or a group —C(O)—$C_1$–$C_{18}$alkyl or a group —O—CH$_2$—CH(OH)—CH$_2$—NR$_{12}$R$_{13}$, with $R_{12}$ and $R_{13}$ being $C_1$–$C_{18}$alkyl or together form a 4 to 8 membered ring as defined in claim 1, or D is a group —O—CH$_2$—CH(OH)—CH$_2$—N($R_{12}$)—CH$_2$—CHOH—CH$_2$—O— or —O—CH$_2$—CH(OH)—CH$_2$—W—CH$_2$—CHOH—CH$_2$—O— with W being a divalent amino group (—N($C_1$–$C_{18}$alkyl)—), a polyamine residue, a polyethyleneimine residue or a polyoxyalkyleneamine residue.

3. A colour photographic material according to claim 1, containing a compound of the formula II, wherein $R_2$ is methyl and A is a group —CH$_2$—CHY—CH$_2$—, thus having a structure of the formula IIa

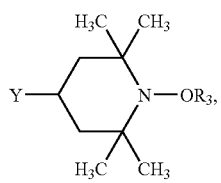

IIa wherein $R_3$ and Y are as defined in claim 1.

4. A colour photographic material according to claim 3, wherein

Y is H, OH, $OR_{14}$, —O—C(O)—$R_{17}$,
$R_{14}$ is $C_1$-$C_{18}$alkyl, phenyl, benzyl, mesityl,
$R_{17}$ is $C_1$-$C_{18}$alkyl, phenyl, benzyl, mesityl,
$R_3$ is a radical —CH($CH_3$)—X—D wherein X is phenylene,
D is a group

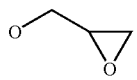

or a group —C(O)—$C_1$-$C_{18}$alkyl or
    a group —O—$CH_2$—CH(OH)—$CH_2$—$NR_{12}R_{13}$, with $R_{12}$ and $R_{13}$ being $C_1$-$C_{18}$alkyl or together form a 4 to 8 membered ring as defined in claim 1, or
D is a group —O—$CH_2$—CH(OH)—$CH_2$—N($R_{12}$)—$CH_2$—CHOH—$CH_2$—O— or —O—$CH_2$—CH(OH)—$CH_2$—W—$CH_2$—CHOH—$CH_2$—O— with W being a divalent amino group (—N($C_1$-$C_{18}$alkyl)—), a polyamine residue, a polyethyleneimine residue or a polyoxyalkyleneamine residue.

5. A colour photographic material according to claim 1, containing a compound of the formula II, wherein A is a group —$CH_2$—C(OZ)(OZ')—$CH_2$—, thus having a structure of the formula IIb

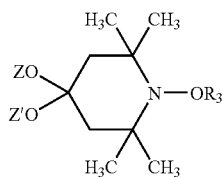

IIb wherein $R_3$, Z and Z' are as defined in claim 1.

6. A colour photographic material according to claim 5, wherein $R_3$ is a radical —CH($CH_3$)—X—D wherein X is phenylene,
D is a group

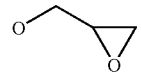

or a group —C(O)—$C_1$-$C_{18}$alkyl or
    a group —O—$CH_2$—CH(OH)—$CH_2$—$NR_{12}R_{13}$, with $R_{12}$ and $R_{13}$ being $C_1$-$C_{18}$alkyl or together form a 4 to 8 membered ring as defined in claim 1, or
D is a group —O—$CH_2$—CH(OH)—$CH_2$—N($R_{12}$)—$CH_2$—CHOH—$CH_2$—O— or —O—$CH_2$—CH(OH)—$CH_2$—W—$CH_2$—CHOH—$CH_2$—O— with W being a divalent amino group (—N($C_1$-$C_{18}$alkyl)—), a polyamine residue, a polyethyleneimine residue or a polyoxyalkyleneamine residue.

7. A method of providing resistance to light or dark fade of photographic dyes by incorporating compounds of the formula I or II as defined in claim 1 in the dye providing light-sensitive layers, in a quantity of 0.1 to 2 mol/mol of color coupler.

8. A method according to claim 7 of providing resistance to light or dark fade of photographic dyes by incorporating compounds of the formula I or II as defined in claim 1 in the dye providing light-sensitive layers in a quantity of 0.1 to 0.5 mol/mol of color coupler.

9. A method according to claim 7 of providing resistance to light or dark fade of photographic dyes by incorporating compounds of the formula I or II as defined in claim 1 in the yellow dye providing blue light-sensitive layer.

10. A dye providing light-sensitive photographic layer comprising at least one of the compounds of the formula I or II according to claim 1 in a quantity of 0.1 to 2 mol/mol of color coupler.

11. A dye providing light-sensitive photographic layer comprising at least one of the compounds of the formula I or II according to claim 1 in a quantity of 0.1 to 0.5 mol/mol of color coupler.

12. A yellow dye providing blue light-sensitive photographic layer comprising at least one of the compounds of the formula I or II according to claim 1 in a quantity of 0.1 to 2 mol/mol of color coupler.

* * * * *